(12) United States Patent
Miracle et al.

(10) Patent No.: US 11,946,018 B2
(45) Date of Patent: *Apr. 2, 2024

(54) FRESHENING COMPOSITIONS WITH ETHOXYLATED/PROPOXYLATED AROMATICS

(71) Applicant: The Procter & Gamble Company, Cincinnati, OH (US)

(72) Inventors: Gregory Scot Miracle, Liberty Township, OH (US); Michael David O'Young Mui, Mason, OH (US); Kevin Lee Kott, Cincinnati, OH (US); George Kavin Morgan, III, Hamilton, OH (US); Jennifer Lea Rinker, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/864,176

(22) Filed: May 1, 2020

(65) Prior Publication Data

US 2020/0353114 A1    Nov. 12, 2020

Related U.S. Application Data

(60) Provisional application No. 62/845,896, filed on May 10, 2019.

(51) Int. Cl.
| | | |
|---|---|---|
| *C11D 1/722* | (2006.01) | |
| *A61L 2/22* | (2006.01) | |
| *A61L 9/01* | (2006.01) | |
| *A61L 9/14* | (2006.01) | |
| *C11B 9/00* | (2006.01) | |
| *C11D 1/72* | (2006.01) | |
| *C11D 1/94* | (2006.01) | |
| *C11D 3/20* | (2006.01) | |
| *C11D 3/50* | (2006.01) | |

(52) U.S. Cl.
CPC ............. *C11B 9/0003* (2013.01); *A61L 2/22* (2013.01); *A61L 9/01* (2013.01); *A61L 9/14* (2013.01); *C11D 1/72* (2013.01); *C11D 1/722* (2013.01); *C11D 1/94* (2013.01); *C11D 3/2003* (2013.01); *C11D 3/2041* (2013.01); *C11D 3/2062* (2013.01); *C11D 3/2065* (2013.01); *C11D 3/2068* (2013.01); *C11D 3/50* (2013.01); *A61L 2202/26* (2013.01)

(58) Field of Classification Search
CPC .. C11D 1/72; C11D 1/722; C11D 3/50; C11D 3/505; C11D 7/261; C11D 7/263; C11D 7/5004; C11D 9/44; C11D 11/0017; C11D 17/0021; C11D 7/5081

See application file for complete search history.

(56) References Cited

U.S. PATENT DOCUMENTS

| | | | |
|---|---|---|---|
| 7,179,775 B2 * | 2/2007 | Foster | C11D 7/14 510/435 |
| 7,550,416 B2 | 6/2009 | Woo | |
| 9,260,817 B2 | 2/2016 | Williams | |
| 9,511,165 B2 | 12/2016 | Vlad | |
| 2005/0124512 A1 | 6/2005 | Woo | |
| 2015/0217015 A1 * | 8/2015 | Williams | C11D 3/0068 424/76.21 |
| 2015/0252302 A1 * | 9/2015 | Rieth | A61Q 19/00 8/405 |
| 2016/0067661 A1 | 3/2016 | Ahrens | |
| 2016/0096192 A1 * | 4/2016 | Bush | B08B 1/006 118/712 |
| 2016/0333291 A1 * | 11/2016 | Aida | A61Q 13/00 |
| 2017/0137745 A1 * | 5/2017 | Tang | C11D 1/146 |
| 2017/0247110 A1 | 8/2017 | Chappell | |
| 2017/0274110 A1 | 9/2017 | Nwachukwu | |
| 2018/0155658 A1 * | 6/2018 | Lant | C11D 3/0021 |
| 2019/0093047 A1 | 3/2019 | Yoshida | |
| 2019/0194579 A1 * | 6/2019 | Miracle | C11D 3/42 |
| 2020/0353113 A1 * | 11/2020 | Mui | A61K 8/86 |

FOREIGN PATENT DOCUMENTS

| | | |
|---|---|---|
| CN | 1169749 A | 1/1998 |
| CN | 107406802 A | 11/2017 |
| EP | 2708593 A1 | 3/2014 |
| JP | S5770197 A | 4/1982 |
| JP | H10245782 A | 9/1998 |
| JP | 2006328551 A | 12/2006 |
| JP | 2010155992 A | 7/2010 |
| JP | 2010530918 A | 9/2010 |
| JP | 2015509122 A | 3/2015 |
| JP | 2019510567 A | 4/2019 |
| WO | 2014043075 A1 | 3/2014 |

OTHER PUBLICATIONS

All Office Actions; U.S. Appl. No. 16/864,175.
Case AA1349 Search Report; Serial No. PCT/US2020/070034; 12 Pages; dated Aug. 7, 2020.
Case AA1350 Search Report; Serial No. PCT/US2020/070035; 12 Pages; dated Aug. 7, 2020.
"Dow Oxygenated Solvents", Product Overview and Selection Guide, 2018, 8 pages.
DOWANOL™ EPh Glycol Ether, Form No. 110-00591-0308, Mar. 2008, 2 pages.
Dow produces a wide range of glycol ether products consisting of P-Series glycol ethers and acetates (from propylene oxide) and E-Series glycol ethers and cetates (from ethylene oxide).2Pages.
U.S. Appl. No. 16/864,175, filed May 1, 2020, Mui, et al.

* cited by examiner

*Primary Examiner* — Charles I Boyer

(74) *Attorney, Agent, or Firm* — Carolyn S. Powell; George H. Leal

(57) ABSTRACT

Freshening composition having at least 70% by weight of the freshening composition of water, a perfume, wherein the perfume includes at least 60% by weight of the perfume, Perfume Raw Materials ("PRMs") having C log P greater than 1; and at least 0.0015% by weight of the freshening composition of an alkoxylated aromatic.

19 Claims, No Drawings

FRESHENING COMPOSITIONS WITH ETHOXYLATED/PROPOXYLATED AROMATICS

FIELD OF THE INVENTION

The present invention relates to freshening compositions having alkoxylated aromatics and perfume raw materials (PRMs) in an aqueous carrier for providing freshness benefits.

BACKGROUND OF THE INVENTION

Freshening products for freshening fabrics or the air or reducing/eliminating malodors on fabrics and/or in the air are currently available. These products typically contain a freshening composition that includes perfume raw materials (PRMs), solvents, surfactants, and high levels of water. Having a wide variety of scent choices in freshening products enables consumers to find one that they like.

However, because of the hydrophobic nature of PRMs, surfactants and/or solvents are used to solubilize and emulsify the PRMs, especially given formulations with high levels of water. However, solvents and relatively high levels of surfactants, although help to emulsify particularly hydrophobic PRMs, may pose at least one of several challenges.

For example, although surfactants are used, the levels are to be minimized otherwise the surfactants may cause fabrics or surfaces to turn yellow or brown under natural light and/or make fabric or surfaces susceptible to soiling and/or change the consumer perception of how the fabric or surface feels. Solvent selection and levels are to be considered as they have limited ability to solubilize a wide range of PRMs, have environmental considerations, and may negatively impact scent. Additionally, many solvents used are high Volatile Organic Compounds (VOC). VOC materials pose challenges for negatively impacting scent as well as concerns around flash point regulations. Given these challenges, formulators typically have solvent and surfactant limitations, which in turn minimizes the use of relatively more hydrophobic PRMs. This reduces the breadth of available PRMs and thus scent experiences to users. These challenges are exacerbated when formulations contain especially high levels of water and/or high levels of relatively hydrophobic PRMs.

Therefore, there is a need for improved freshening compositions that provide a wide variety of scent experiences enabled by more hydrophobic PRMs while minimizing levels of surfactants.

SUMMARY OF THE INVENTION

The present invention relates to a freshening composition comprising:
a) at least 70% by weight of the freshening composition of water;
b) a perfume, wherein the perfume comprises at least 60% by weight of the perfume, Perfume Raw Materials having C log P greater than 1; and
c) at least 0.0015% by weight of the freshening composition of an alkoxylated aromatic;
wherein the alkoxylated aromatic is according to Formula (I):

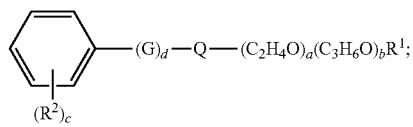

wherein the index d is 0 or 1, and G is selected from $C_1$-$C_4$ alkylene;
wherein Q is selected from O, S, and $NR^3$, where $R^3$ is selected from the group consisting of H, $C_1$-$C_{15}$ alkyl, and $(C_2H_4O)_e(C_3H_6O)_fR^4$;
wherein a, e individually is a value selected from 1 to 30; b, f individually is a value selected from 0-15;
wherein the value of a+b, the degree of alkoxylation, is from 3 to 30 when Q is O, S or $NR^3$ and $R^3$ is H or $C_1$-$C_{15}$ alkyl,
wherein the value of a+b, the degree of alkoxylation, is from 1 to 20 when Q is $NR^3$ and $R^3$ is $(C_2H_4O)_e(C_3H_6O)_fR^4$;
wherein the value of e+f, the degree of alkoxylation, is from 1 to 20 when Q is $NR^3$ and $R^3$ is $(C_2H_4O)_e(C_3H_6O)_fR^4$;
wherein $R^1$, $R^4$ is independently selected from H and $C_1$-$C_4$ alkyl;
wherein c is a value selected from 0 to 5;
wherein each $R^2$ is independently selected from $C_1$-$C_4$ alkyl, $C_1$-$C_4$ alkoxy, and wherein any two vicinal $R^2$ may combine to make an aliphatic or aromatic fused ring;
wherein when Q is O and $R^1$ is H, at least one of c or d is greater than 0.

DETAILED DESCRIPTION

Perfume raw materials (PRMs) are typically formulated with water to make sprayable freshening compositions including but not limited to air freshening compositions, fabric freshening compositions or air and fabric freshening compositions. However, because of the hydrophobic nature of PRMs, solvents and/or surfactants are used to solubilize and emulsify the PRMs in compositions with high water content. Solvents suitable for solubilizing PRMs typically include alcohols, polyols and mixtures thereof.

The present invention is based on the surprising discovery that the freshening composition of the present invention comprising high levels of water, perfume and relatively low levels of alkoxylated aromatic can improve solubility of a perfume having PRMs having a C log P greater than 1.0 in water content thereby providing phase stable sprayable freshening compositions.

Having the combination of PRMs and alkoxylated aromatic enables a phase stable sprayable freshening composition and a wider range of PRMs may be formulated.

In the following description, the composition described is a fabric freshening composition. However, it is contemplated that the composition may be configured for use in a variety of applications to provide freshness on inanimate surfaces or in the air.

Prior to describing the present invention in detail, the following terms are defined for clarity. Terms not defined should be given their ordinary meaning as understood by a skilled person in the relevant art.

The term "freshening composition" as used herein refers to compositions for providing freshness on surfaces including inanimate surfaces or in the air.

The term "inanimate surface" as used herein refers to surfaces including but not limited to fabrics, carpets, household surfaces such as countertops, floors, garbage cans, ceilings, walls, carpet padding, air filters, and the like.

The term "C log P" as used herein refers to a calculated log P ("C log P") value of a perfume raw material (hereinafter "PRM"). An octanol/water partition coefficient of a PRM is the ratio between its equilibrium concentrations in octanol and in water. The partition coefficients of the PRM used in a freshening composition may more conveniently be given in the form of its logarithm to the base 10, Log P. The C log P is determined by a model that computes the octanol-water partition coefficient (log P or log Kow) for general organic molecules based directly on molecular structure. Log P is a measure of the distribution of a solute between two immiscible liquid phases, octanol and water, and is generally used as a relative measure of the hydrophobicity of a solute. One way of computing Log P of a PRM is using the ACD/Labs Log P software module from Advanced Chemistry Development, Inc. Details of the calculation of log P can be found on the ACD/Labs website (https://www.acdlabs.com/products/percepta/predictors/logp/). Log P values of PRMs calculating using the ACD/Labs Log P software module and the Log P values of PRMs are used in the selection of PRMs which are useful in the present invention as described hereafter in the Examples. However, it will be appreciated that another suitable way of measuring Log P is using the "C log P" program from BioByte Corp (e.g., C log P Version 4.0 and Manual 1999). CLOG P USER GUIDE, Version 4.0, BioByte Corp (1999) (http://www.bio-byte.com/bb/prod/clogp40.html). A further suitable way of measuring Log P is using CLOGP program from Daylight Chemical Information Systems, Inc. of Alison Viejo, CA The CLOGP Reference manual, Daylight Version 4.9, Release Date Jan. 2, 2008.

The term "sulfur-containing pro-perfume" as used herein refers to a type of pro-perfume compound that contains sulfur. The term "pro-perfume" as used herein refers to compounds resulting from the reaction of PRMs with other chemicals, which have a covalent bond between one or more PRMs and these chemicals. The PRM is converted into a new material called a pro-perfume compound, which then may release the original PRM (i.e. pre-converted) upon exposure to a trigger such as water or light or atmospheric oxygen. Suitable pro-perfume compounds and methods of making the same can be found in U.S. Pat. Nos. 7,018,978; 6,861,402; 6,544,945; 6,093,691; 6,165,953; and 6,096,918.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

I. Freshening Composition

A freshening composition according to the present invention comprises water in a level of at least 85% by weight of the composition, alkyoxylated aromatic in a level of at least 0.0015% by weight of the composition, and a perfume wherein the perfume comprises at least 60% by weight of perfume, of Perfume Raw Material(s) having a C log P greater than 1.0. A technical effect of providing the alkoxylated aromatic is that the perfume with at least 60% of PRMs have a C log P greater than 1 may be formulated with high levels of water (at least 85%) to provide a freshening composition. The freshening composition is sprayable and the perfume remains solubilized to provide a phase-stable freshening composition that provides a consistent delivery of scent freshness in each spray.

Without wishing to be bound by theory, use of alkoxylated aromatics relative to use of traditional solvents such as ethanol to solubilize perfumes in freshening compositions is alkoxylated aromatics have the combination of a benzene containing functional group and an alkoxy functional group in the same molecule which provides unique solvency characteristics with both polar and non-polar properties. This surfactant-like structure gives alkoxylated aromatics the ability to couple unlike liquid phases of ingredients used for freshening compositions (e.g. water and perfume as described hereinafter) and be miscible in a broad range of hydrophilic and hydrophobic solvents. It will be appreciated by a person skilled in the art that amounts of the alkoxylated aromatics and the PRMs, and water may be configured to meet performance requirements as defined under Test Methods including Test Method for Measurement of Turbidity described hereinafter. In particular, it will be appreciated that the freshening composition may be configured with PRMs having C log P greater than 1 at a low enough level with at least 0.0015% of an alkoxylated aromatic to meet the above performance requirements.

It will be appreciated by a person skilled in the art that amounts of the alkoxylated aromatics and the PRMs, and water may be configured to meet performance requirements as defined under Test Methods including Test Method for Measurement of Turbidity described hereinafter. In particular, it will be appreciated that the freshening composition may be configured with PRMs having C log P greater than 1 at a low enough level with at least 0.0015% of alkoxylated aromatic to meet the above performance requirements.

Components of a freshening composition of the present invention are described in the following paragraphs.

A. Water

A freshening composition of the present invention may comprise at least 70%, by weight of the composition of water. The water may be in an amount from 70% to 99.5%, from 90% to 99.5%, from 95% to 99.5%, 95%, or different combinations of the upper and lower percentages described above or combinations of any integer in the ranges listed above, of water by weight of the composition. The water may be distilled, deionized or tap water. Having high levels of water enable a sprayable freshening composition while minimizing any visible residues and/or stains on fabric articles.

B. Alkoxylated Aromatics

The freshening composition comprises an alkoxylated aromatic in a level of at least 0.0015% by weight of the composition. Alkoxylation is a chemical reaction that involves the addition of an epoxide which is an alkoxylating agent to another compound. Epoxides may be lower molecular weight epoxides (oxiranes) such as ethylene oxide, propylene oxide and butylene oxide. These epoxides are capable of reacting with a hydroxyl group generally under base catalysis, causing a ring opening and the addition of an oxyalkylene group. The resulting compound contains a hydroxyl group, so a varied number of moles of oxide can be added. Alkoxylation of a benzene-containing compound relates to the reaction of mixtures of an epoxide with the aromatic containing compound which produces alkoxylated aromatics.

The alkoxylated aromatic comprises a structure according to Formula (I):

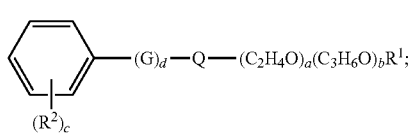

wherein the index d is 0 or 1, and G is selected from $C_1$-$C_4$ alkylene;
wherein Q is selected from O, S, and $NR^3$, where $R^3$ is selected from the group consisting of H, $C_1$-$C_{15}$ alkyl, and $(C_2H_4O)_e(C_3H_6O)_fR^4$;
wherein a, e individually is a value selected from 1 to 30; b, f individually is a value selected from 0-15;
wherein the value of a+b, the degree of alkoxylation, is from 3 to 30 when Q is O, S or $NR^3$ and $R^3$ is H or $C_1$-$C_{15}$ alkyl,
wherein the value of a+b, the degree of alkoxylation, is from 1 to 20 when Q is $NR^3$ and $R^3$ is $(C_2H_4O)_e(C_3H_6O)_fR^4$;
wherein the value of e+f, the degree of alkoxylation, is from 1 to 20 when Q is $NR^3$ and $R^3$ is $(C_2H_4O)_e(C_3H_6O)_fR^4$;
wherein $R^1$, $R^4$ is independently selected from H and $C_1$-$C_4$ alkyl;
wherein c is a value selected from 0 to 5;
wherein each $R^2$ is independently selected from $C_1$-$C_4$ alkyl, $C_1$-$C_4$ alkoxy, and wherein any two vicinal $R^2$ may combine to make an aliphatic or aromatic fused ring;
wherein when Q is O and $R^1$ is H, at least one of c or d is greater than 0.

Each of the a units of $(C_2H_4O)$ and b units of $(C_3H_6O)$ may be present in any order. Each of the e units of $(C_2H_4O)$ and f units of $(C_3H_6O)$ may also be present in any order.

It will be appreciated that the alkoxylated aromatic may be a mixture of compounds, wherein one or more compounds has a structure according to Formula (I). Further, at least two, preferably at least three, more preferably at least four, even more preferably at least five compounds of the mixture of compounds may each have a structure according to Formula (I) and comprise at least 5% by the total weight of the mixture of compounds. It will be appreciated by a skilled person that Gas Chromatography/Mass Spectrometry (GC/MS) methods may be used to determine the individual ethoxylate or propoxylate species in an alkoxylated aromatic.

The ethoxylate or propoxylate groups may be in any order; preferably the value of a is greater than the value of b, more preferably the value of a is greater than 2.5 times, 5 times, or even 9 times the value of b.

The alkoxylated aromatic may be selected from the group consisting of: ethoxylated aromatic, ethoxylated-propoxylated aromatic and combinations thereof, preferably ethoxylated aromatic.

When Q is O; preferably G is $CH_2$ when d is 1; preferably when d is 1, the index c is 0, 1 or 2; preferably when d is 0, the index c is 1 or 2; preferably when the index c is 1, $R^2$ is $C_1$ alkyl or $C_1$ alkoxy, and when c is 2, two vicinal groups combine to form a fused $C_6$ aromatic ring.

i. Ethoxylated Cresol

The alkoxylated aromatic may be an ethoxylated cresol. The ethoxylated cresol may comprise a structure according to Formula (II),

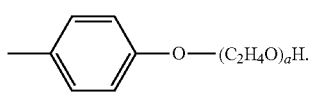

The ethoxylated cresol may comprise a structure according to Formula (III),

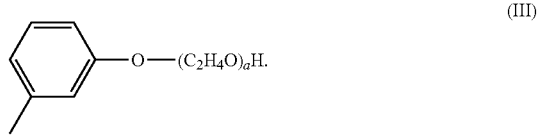

The ethoxylated cresol may comprise a structure according to Formula (IV),

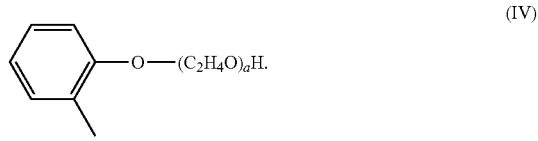

ii. Ethoxylated Cresyl Alkyl Ether

The alkoxylated aromatic may be an ethoxylated cresyl alkyl ether. The ethoxylated cresyl alkyl ether may comprise a structure according to Formula (V),

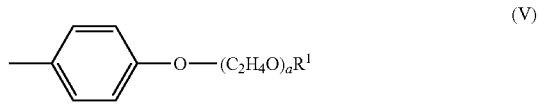

The ethoxylated cresyl alkyl ether may comprise a structure according to Formula (VI),

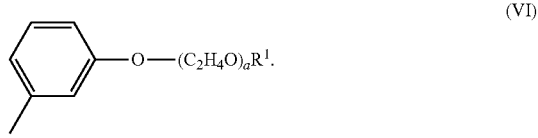

The ethoxylated cresyl alkyl ether may comprise a structure according to Formula (VII),

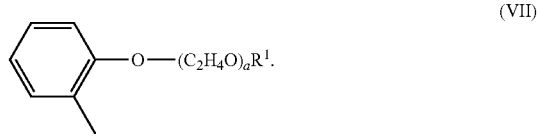

iii. Alkoxylated Cresyl Alkyl Ether

The alkoxylated aromatic may be an alkoxylated cresyl ether. The alkoxylated cresyl alkyl ether may comprise a structure according to Formula (VIII),

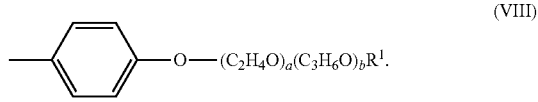

The alkoxylated cresyl ether may comprise a structure according to Formula (IX),

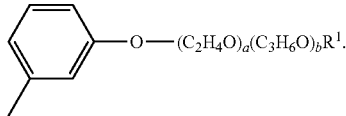

(IX)

The alkoxylated cresyl ether may comprise a structure according to Formula (X),

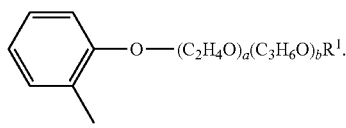

(X)

iv. Ethoxylated Napthol

The alkoxylated aromatic may be an ethoxylated napthol. The ethoxylated napthol may comprise a structure according to Formula (XI), (XI)

vi. Alkoxylated Napthyl Alky Ether

The alkoxylated aromatic may be an alkoxylated napthyl alkyl ether and comprise a structure according to Formula (XIII),

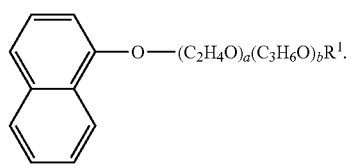

(XIII)

vii. Alkoxylated Naphthol

The alkoxylated aromatic may be an alkoxylated naphthol wherein a and b are non-zero and R1 is H in Formula (XIII) above.

viii. Ethoxylated Benzyl Alcohol

The alkoxylated aromatic may be an ethoxylated benzyl alcohol. The ethoxylated benzyl alcohol may comprise a structure according to Formula (XIV),

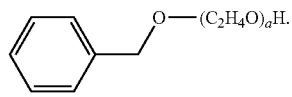

(XIV)

Further non-limiting alkoxylated aromatics are described in U.S. Patent Publication No. US2016/0067661A1.

Still further, exemplary alkoxylated aromatics which are commercially available are listed in Table 1 below.

TABLE 1

| Alkoxylated Aromatic | CAS No. | Commercially Available from |
|---|---|---|
| Ethoxylated Naphthol | 335545-57-4 | Parchem - fine & specialty chemicals https://www.parchem.com/chemical-supplier-distributor/Ethoxylated-naphthol-023892.aspx |
| Ethoxylated Cresol | 37281-57-5 | Parchem - fine & specialty chemicals https://www.parchem.com/chemical-supplier-distributor/Ethoxylated-cresol-024044.aspx |
| Ethoxylated Benzyl Alcohol | 26403-74-7 | Trade name: Genapol BA040 Clariant https://www.clariant.com/en/Solutions/Products/2013/12/09/18/27/Genapol-BA-040 | v. Ethoxylated Napthyl Alkyl Ether

The alkoxylated aromatic may be an ethoxylated napthyl alkyl ether, and comprise a structure according to Formula (XII),

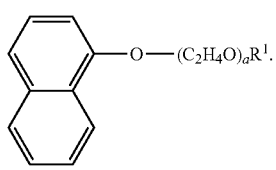

(XII)

The alkoxylated aromatic may be in an amount of at least 0.0015%, preferably from 0.0015% to (9q) %, 0.0015% to (3.5q) %, more preferably, 0.0015% to (2q) %, even more preferably 0.0015% to (1.5q) %, by weight of the freshening composition, wherein q is a ratio defined as $q=[(\text{average MW})/(358 \text{ daltons})]$, wherein (average MW)=average molecular weight of the alkoxylated aromatic (daltons).

The alkoxylated aromatic may be in an amount of at least 0.0015%, from 0.0015% to 18%, 0.0015% to 7%, 0.0015% to 4%, 0.0015% to 3%, or different combinations of the upper and lower percentages described above or combinations of any integer in the ranges listed above by weight of the freshening composition.

C. Perfume Composition (Hereinafter "Perfume")

The freshening composition comprises a perfume formulated in an effective amount such that it provides a desired scent characteristic and can be homogenously solubilized in the freshening composition to deliver a consistent release profile. The perfume comprises at least 60% by weight of the perfume of Perfume Raw Materials (PRMs) having a C log P value greater than 1. The perfume may be in an amount of at least 0.001%, from 0.002% to 3%, from 0.005% to 1%, from 0.005% to 0.4%, or different combinations of the upper and lower percentages described above or combinations of any integer in the ranges listed above by weight of the freshening composition.

The C log P values may be defined by four groups and the PRMs may be selected from one or more of these C log P groups. The first group comprises PRMs that have a B.P. of about 250° C. or less and C log P of about 3 or less. Exemplary PRMs of the first group include, but are not limited to, PRMs as shown in Table 2 below.

TABLE 2

Examples of First Group of PRMs

| Perfume Raw Material (PRM) Name | IUPAC Name | CAS Number | Boiling Point, BP (° C.) | ClogP |
|---|---|---|---|---|
| Allyl Caproate | prop-2-enyl hexanoate | 128-68-2 | 185 | 2.772 |
| Amyl Acetate | pentyl acetate | 628-63-7 | 142 | 2.258 |
| Amyl Propionate | pentyl propanoate | 624-54-4 | 161 | 2.657 |
| Anisic Aldehyde | 4-methoxybenzaldehyde | 123-11-5 | 248 | 1.779 |
| Anisole | Anisole | 100-66-3 | 154 | 2.061 |
| Benzaldehyde | Benzaldehyde | 100-52-7 | 179 | 1.48 |
| Benzyl Acetate | Benzyl Acetate | 140-11-4 | 215 | 1.96 |
| Benzyl Acetone | 4-phenylbutan-2-one | 2550-26-7 | 235 | 1.739 |
| Benzyl Alcohol | phenylmethanol | 100-51-6 | 205 | 1.1 |
| Benzyl Formate | Benzyl Formate | 104-57-4 | 202 | 1.414 |
| Benzyl Iso Valerate | 2-phenylethyl 3-methylbutanoate | 140-26-1 | 246 | 2.887 |
| Benzyl Propionate | Benzyl Propionate | 122-63-4 | 222 | 2.489 |
| Beta Gamma Hexenol | (Z)-hex-3-en-1-ol | 928-96-1 | 157 | 1.337 |
| Camphor Gum | (1R,4S)-1,7,7-trimethylbicyclo[2.2.1]heptan-2-one | 464-48-2 | 208 | 2.117 |
| laevo-Carveol | 2-methyl-5-prop-1-en-2-ylcyclohex-2-en-1-ol | 99-48-9 | 227 | 2.265 |
| d-Carvone | (5S)-2-methyl-5-prop-1-en-2-ylcyclohex-2-en-1-one | 2244-16-8 | 231 | 2.01 |
| laevo-Carvone | (5R)-2-methyl-5-prop-1-en-2-ylcyclohex-2-en-1-one | 6485-40-1 | 230 | 2.203 |
| Cinnamyl Formate | [(E)-3-phenylprop-2-enyl] formate | 104-65-4 | 250 | 1.908 |
| Cis-Jasmone | 3-methyl-2-[(Z)-pent-2-enyl]cyclopent-2-en-1-one | 488-10-8 | 248 | 2.712 |
| Cis-3-Hexenyl Acetate | [(Z)-hex-3-enyl] acetate | 3681-71-8 | 169 | 2.243 |
| Cis-6-Nonen-1-OL FCC | (Z)-non-6-en-1-ol | 35854-86-5 | 214.2 | 2.52 |
| Cuminic alcohol | (4-propan-2-ylphenyl)methanol | 536-60-7 | 248 | 2.531 |
| Cuminic aldehyde | 4-propan-2-ylbenzaldehyde | 122-03-2 | 236 | 2.78 |
| Cyclal C | 3,5-dimethylcyclohex-3-ene-1-carbaldehyde | 68039-48-5 | 180 | 2.301 |
| Dimethyl Benzyl Carbinol | 2-methyl-1-phenylpropan-2-ol | 100-86-7 | 215 | 1.891 |
| Dimethyl Benzyl Carbinyl Acetate | (2-methyl-1-phenylpropan-2-yl) acetate | 151-05-3 | 250 | 2.797 |
| Ethyl Acetate | Ethyl Acetate | 141-78-6 | 77 | 0.73 |
| Ethyl Benzoate | Ethyl Benzoate | 93-89-0 | 212 | 2.64 |
| Ethyl Hexyl Ketone | nonan-3-one | 925-78-0 | 190 | 2.916 |
| Ethyl-2-methyl butyrate | ethyl 2-methylbutanoate | 7452-79-1 | 131 | 2.1 |
| Ethyl-2-Methyl Pentanoate | ethyl 2-methylpentanoate | 39255-32-8 | 143 | 2.7 |
| Ethyl Phenyl Acetate | ethyl 2-phenylacetate | 101-97-3 | 229 | 2.489 |
| Eucalyptol | 1,3,3-trimethyl-2-oxabicyclo[2.2.2]octane | 470-82-6 | 176 | 2.756 |
| Fenchyl Alcohol | 1,3,3-trimethylbicyclo[2.2.1]heptan-2-ol | 1632-73-1 | 200 | 2.579 |
| Hexyl Acetate | Hexyl Acetate | 142-92-7 | 172 | 2.787 |
| Hexyl Formate | Hexyl Formate | 629-33-4 | 155 | 2.381 |
| Hydratropic Alcohol | 2-phenylpropan-1-ol | 1123-85-9 | 219 | 1.582 |

TABLE 2-continued

Examples of First Group of PRMs

| Perfume Raw Material (PRM) Name | IUPAC Name | CAS Number | Boiling Point, BP (° C.) | ClogP |
|---|---|---|---|---|
| Hydroxycitronellal | 7-hydroxy-3,7-dimethyloctanal | 107-75-5 | 241 | 1.541 |
| Isoamyl Alcohol | 3-methylbutan-1-ol | 123-51-3 | 132 | 1.222 |
| Isomenthone | 5-methyl-2-propan-2-ylcyclohexan-1-one | 89-80-5 | 210 | 2.831 |
| Isopulegyl Acetate | (5-methyl-2-prop-1-en-2-ylcyclohexyl) acetate | 89-49-6 | 239 | 2.1 |
| Isoquinoline | Isoquinoline | 119-65-3 | 243 | 2.08 |
| Ligustral | 2,4-dimethylcyclohex-3-ene-1-carbaldehyde | 68039-49-6 | 177 | 2.301 |
| Linalool | 3,7-dimethylocta-1,6-dien-3-ol | 78-70-6 | 198 | 2.429 |
| Linalyl Formate | 3,7-dimethylocta-1,6-dien-3-yl formate | 115-99-1 | 202 | 2.929 |
| Menthone | 5,5-dimethylcyclohexane-1,3-dione | 126-81-8 | 207 | 2.65 |
| Methyl Amyl Ketone | heptan-2-one | 110-43-0 | 152 | 1.848 |
| Methyl Anthranilate | methyl 2-aminobenzoate | 134-20-3 | 237 | 2.024 |
| Methyl Benzoate | Methyl Benzoate | 93-58-3 | 200 | 2.111 |
| Methyl Eugenol | 1,2-dimethoxy-4-prop-2-enylbenzene | 93-15-2 | 249 | 2.783 |
| Methyl Heptenone | 6-methylhept-5-en-2-one | 110-93-0 | 174 | 1.703 |
| Methyl Heptine Carbonate | methyl oct-2-ynoate | 111-12-6 | 217 | 2.528 |
| Methyl Heptyl Ketone | nonan-2-one | 821-55-6 | 194 | 1.823 |
| Methyl Hexyl Ketone | octan-2-one | 111-13-7 | 173 | 2.377 |
| Methyl Phenyl Carbinyl Acetate | 1-phenylethyl acetate | 93-92-5 | 214 | 2.269 |
| Nerol | (2Z)-3,7-dimethylocta-2,6-dien-1-ol | 106-25-2 | 227 | 2.649 |
| OCTAHYDRO-COUMARIN | octahydro-2H-chromen-2-one | 4430-31-3 | 222.9 | 1.58 |
| Octyl Alcohol (Octanol-2) | octan-2-ol | 123-96-6 | 179 | 2.719 |
| para-Methyl Acetophenone | 1-(4-methylphenyl)ethenone | 122-00-9 | 228 | 2.08 |
| Phenoxy Ethanol | 1-phenoxyethanol | 56101-99-6 | 245 | 1.188 |
| Phenyl Acetaldehyde | 2-phenylacetaldehyde | 122-78-1 | 195 | 1.78 |
| Phenyl Acetaldehyde Dimethyl Acetal | (2,2-dimethoxyethyl)benzene | | 249.5 | 2.15 |
| Phenyl Ethyl Acetate | 2,2-dimethoxyethylbenzene | 101-48-4 | 232 | 2.129 |
| Phenyl Ethyl Alcohol | 2-phenylethanol | 60-12-8 | 220 | 1.183 |
| Phenyl Ethyl Dimethyl Carbinol | 2-methyl-4-phenylbutan-2-ol | 103-05-9 | 238 | 2.42 |
| Prenyl Acetate | 3-methylbut-2-enyl acetate | 1191-16-8 | 155 | 1.684 |
| Propyl Butyrate | propyl butanoate | 105-66-8 | 143 | 2.21 |
| Pulegone | 5-methyl-2-propan-2-ylidenecyclohexan-1-one | 15932-80-6 | 224 | 2.35 |
| Rose Oxide | 4-methyl-2-(2-methylprop-1-enyl)oxane | 16409-43-1 | 182 | 2.896 |
| 4-Terpinenol | 4-methyl-1-propan-2-ylcyclohex-3-en-1-ol | 562-74-3 | 212 | 2.749 |
| alpha-Terpineol | 2-(4-methylcyclohex-3-en-1-yl)propan-2-ol | 98-55-5 | 219 | 2.569 |
| Viridine | 2,2-dimethoxyethylbenzene | 101-48-4 | 221 | 1.293 |
| Violiff | (Z)-cyclooct-4-en-1-yl methyl carbonate | 87731-18-8 | 214.4 | 2.79 |

The second group comprises PRMs that have a B.P. of 250° C. or less and C log P of 3.0 or more. Exemplary PRMs of the second group which may be used include, but are not limited to, PRMs as shown in Table 3 below.

TABLE 3

Examples of Second Group of PRMs

| Perfume Raw Material (PRM) Name | IUPAC Name | CAS No. | Boiling Point, BP (° C.) | ClogP |
|---|---|---|---|---|
| allo-Ocimene | (4E,6E)-2,6-dimethylocta-2,4,6-triene | 673-84-7 | 192 | 4.362 |
| Anethol | 1-methoxy-4-[(E)-prop-1-enyl]benzene | 104-46-1 | 236 | 3.314 |
| Benzyl Butyrate | benzyl butanoate | 103-37-7 | 240 | 3.698 |
| Camphene | 2,2-dimethyl-3-methylidenebicyclo[2.2.1]heptane | 79-92-5 | 159 | 4.192 |
| Carvacrol | 2-methyl-5-propan-2-ylphenol | 499-75-2 | 238 | 3.401 |
| cis-3-Hexenyl Tiglate | [(Z)-hex-3-enyl] (E)-2-methylbut-2-enoate | 67883-79-8 | 101 | 3.7 |
| cis Ocimene | (E)-3,7-dimethylocta-1,3,6-triene | — | 156.7 | 4.26 |
| CITRAL DIMETHYL ACETAL | (E)-1,1-dimethoxy-3,7-dimethylocta-2,6-diene | 7549-37-3 | 235.6 | 3.61 |
| Citral (Neral) | (2E)-3,7-dimethylocta-2,6-dienal | 5392-40-5 | 228 | 3.12 |
| Citronellol | 3,7-dimethyloct-6-en-1-ol | 106-22-9 | 225 | 3.193 |
| Citronellyl Acetate | 3,7-dimethyloct-6-enyl acetate | 150-84-5 | 229 | 3.67 |
| Citronellyl Isobutyrate | 3,7-dimethyloct-6-enyl 2-methylpropanoate | 97-89-2 | 249 | 4.937 |
| Citronellyl Nitrile | 3,7-dimethyloct-6-enenitrile | 51566-62-2 | 225 | 3.094 |
| Cyclohexyl Ethyl Acetate | 2-cyclohexylethyl acetate | 21722-83-8 | 187 | 3.321 |
| Decyl Aldehyde | Decanal | 112-31-2 | 209 | 4.008 |
| DECENAL (TRANS-4) | (E)-dec-4-enal | 30390-50-2 | 214.7 | 3.60 |
| Dihydro Myrcenol | 2-methyl-6-methylideneoctan-2-ol | 18479-59-9 | 208 | 3.03 |
| Fenchyl Acetate | (1,3,3-trimethyl-2-bicyclo[2.2.1]heptanyl) acetate | 4057-31-2 | 220 | 3.485 |
| gamma Methyl Ionone | (Z)-3-methyl-4-(2,6,6-trimethylcyclohex-2-en-1-yl)but-3-en-2-one | 127-51-5 | 230 | 4.089 |
| gamma-Nonalactone | 5-pentyloxolan-2-one | 104-61-0 | 243 | 3.14 |
| Geraniol | (E)-3,7-dimethylocta-2,6-dien-1-ol | 106-24-1 | 224.8 | 3.41 |
| Geranyl Acetate | [(2E)-3,7-dimethylocta-2,6-dienyl] acetate | 105-87-3 | 245 | 3.715 |
| Geranyl Formate | [(2E)-3,7-dimethylocta-2,6-dienyl] formate | 105-86-2 | 216 | 3.269 |
| Geranyl Isobutyrate | [(2E)-3,7-dimethylocta-2,6-dienyl] 2-methylpropanoate | 2345-26-8 | 245 | 4.393 |
| Geranyl Nitrile | (2E)-3,7-dimethylocta-2,6-dienenitrile | 5146-66-7 | 222 | 3.139 |
| Hexyl Neopentanoate | hexyl 2,2-dimethylpropanoate | 5434-57-1 | 224 | 4.374 |
| Hexyl Tiglate | hexyl (E)-2-methylbut-2-enoate | 16930-96-4 | 231 | 3.8 |
| alpha-Ionone | (E)-4-(2,6,6-trimethylcyclohex-2-en-1-yl)but-3-en-2-one | 127-41-3 | 237 | 3.381 |
| beta-Ionone | (E)-4-(2,6,6-trimethylcyclohexen-1-yl)but-3-en-2-one | 14901-07-6 | 239 | 3.96 |
| gamma-Ionone | (E)-4-(2,2-dimethyl-6-methylidenecyclohexyl)but-3-en-2-one | 79-76-5 | 240 | 3.78 |
| alpha-irone | (E)-4-(2,5,6,6-tetramethylcyclohex-2-en-1-yl)but-3-en-2-one | 79-69-6 | 250 | 3.82 |
| Isobornyl Acetate | (1,7,7-trimethyl-2-bicyclo[2.2.1]heptanyl) acetate | 76-49-3 | 227 | 3.485 |
| Isobutyl Benzoate | 2-methylpropyl benzoate | 120-50-3 | 242 | 3.028 |
| Isononyl Acetate | 3,5,5-trimethylhexyl acetate | 58430-94-7 | 177.7 | 3.46 |
| Isononyl Alcohol | 7-methyloctan-1-ol | 2430-22-0 | 194 | 3.078 |

TABLE 3-continued

Examples of Second Group of PRMs

| Perfume Raw Material (PRM) Name | IUPAC Name | CAS No. | Boiling Point, BP (° C.) | ClogP |
|---|---|---|---|---|
| Isopulegol | (1R,2S,5R)-5-methyl-2-prop-1-en-2-ylcyclohexan-1-ol | 89-79-2 | 212 | 3.33 |
| Lauric Aldehyde | Dodecanal | 112-54-9 | 249 | 5.066 |
| d-Limonene | (4R)-1-methyl-4-prop-1-en-2-ylcyclohexene | 5989-27-5 | 177 | 4.232 |
| Linalyl Acetate | 3,7-dimethylocta-1,6-dien-3-yl acetate | 115-95-7 | 220 | 3.5 |
| 7-Methyloctyl acetate | 7-methyloctyl acetate | 40379-24-6 | 208.8 | 4.25 |
| Menthyl Acetate | (5-methyl-2-propan-2-ylcyclohexyl) acetate | 2230-87-7 | 227 | 3.21 |
| Methyl Chavicol | 1-methoxy-4-prop-2-enylbenzene | 140-67-0 | 216 | 3.074 |
| Methyl Nonyl Acetaldehyde | 2-methylundecanal | 110-41-8 | 232 | 4.846 |
| Myrcene | 7-methyl-3-methylideneocta-1,6-diene | 123-35-3 | 167 | 4.272 |
| Neral | (2Z)-3,7-dimethylocta-2,6-dienal | 5392-40-5 | 228 | 3.12 |
| Neryl Acetate | [(2Z)-3,7-dimethylocta-2,6-dienyl] acetate | 141-12-8 | 231 | 3.555 |
| Nonyl Acetate | nonyl acetate | 143-13-5 | 212 | 4.374 |
| Nonyl Aldehyde | nonanal | 124-19-6 | 212 | 3.479 |
| OCIMENE | (Z)-3,7-dimethylocta-1,3,6-triene | 3338-55-4 | 156.7 | 4.26 |
| Orange Terpenes(d-Limonene) | (4R)-1-methyl -4-prop-1-en-2-ylcyclohexene | 5989-27-5 | 177 | 4.232 |
| para-Cymene | 1-methyl-4-propan-2-ylbenzene | 99-87-6 | 179 | 4.068 |
| Phenyl Ethyl Isobutyrate | ethyl 2-methyl-2-phenylpropanoate | 2901-13-5 | 250 | 3 |
| alpha-Pinene | 2,6,6-trimethylbicyclo[3.1.1]hept-2-ene | 80-56-8 | 157 | 4.122 |
| beta-Pinene | 6,6-dimethyl-2-methylidenebicyclo[3.1.1]heptane | 25719-60-2 | 166 | 4.182 |
| gamma-Terpinene | 1-methyl-4-propan-2-ylcyclohexa-1,4-diene | 99-85-4 | 183 | 4.232 |
| Terpinolene | 1-methyl-4-propan-2-ylidenecyclohexene | 586-62-9 | 184 | 4.232 |
| Terpinyl acetate | 2-(4-methylcyclohex-3-en-1-yl)propan-2-yl acetate | 80-26-2 | 223.7 | 3.91 |
| Tetrahydro Linalool | 3,7-dimethyloctan-3-ol | 78-69-3 | 191 | 3.517 |
| Tetrahydro Myrcenol | 2,6-dimethyloctan-2-ol | 18479-57-7 | 208 | 3.517 |
| Undecenal | undec-2-enal | 1337-83-3 | 223 | 4.053 |
| undecyl aldehyde | undecanal | 112-44-7 | 234.4 | 4.62 |
| undecylenic aldehyde | undec-10-enal | 112-45-8 | 239.1 | 3.97 |
| Veratrol | 1,2-dimethoxybenzene | 91-16-7 | 206 | 3.14 |
| Verdox | (2-tert-butylcyclohexyl) acetate | 88-41-5 | 221 | 4.059 |
| Vertenex | (4-tert-butylcyclohexyl) acetate | 1900-69-2 | 232 | 4.06 |

The third group comprises PRMs that have a B.P. of 250° C. or more and C log P of 3.0 or less. The fourth group comprises PRMs that have a B.P. of 250° C. or more and C log P of 3.0 or more. Exemplary PRMs of the third and fourth groups which may be used include, but are not limited to, PRMs as shown in Table 4 below. The freshening composition may comprise any combination of PRMs from one or more of the first, second, third and fourth groups.

TABLE 4

Examples of Third and Fourth Groups of PRMs

| Perfume Raw Material (PRM) Name | IUPAC Name | CAS No. | Boiling Point, BP (° C.) | ClogP |
|---|---|---|---|---|
| Amber Xtreme | 2,2,6,6,7,8,8-heptamethyldecahydro-2H-indeno[4,5-b]furan | 476332-65-7 | 306.5 | 6.14 |

TABLE 4-continued

Examples of Third and Fourth Groups of PRMs

| Perfume Raw Material (PRM) Name | IUPAC Name | CAS No. | Boiling Point, BP (° C.) | ClogP |
|---|---|---|---|---|
| Amyl Benzoate | pentyl benzoate | 2049-96-9 | 262 | 3.417 |
| Amyl Cinnamate | pentyl (E)-3-phenylprop-2-enoate | 3487-99-8 | 310 | 3.771 |
| Amyl Cinnamic Aldehyde | [(E)-2-[bis[(2E)-3,7-dimethylocta-2,6-dienoxy]methyl]hept-1-enyl]benzene | 67785-69-7 | 285 | 4.324 |
| iso-Amyl Salicylate | 3-methylbutyl 2-hydroxybenzoate | 87-20-7 | 277 | 4.601 |
| Aurantiol | methyl 2-[(7-hydroxy-3,7-dimethyloctylidene)amino]benzoate | 89-43-0 | 450 | 4.216 |
| Benzophenone | diphenylmethanone | 119-61-9 | 306 | 3.12 |
| Benzyl Salicylate | benzyl 2-hydroxybenzoate | 118-58-1 | 300 | 4.383 |
| CARYOPHYLLENE OXIDE | (1R,4R,6R,10S)-4,12,12-trimethyl-9-methylene-5-oxatricyclo[8.2.0.04,6]dodecane | 1139-30-6 | 270.6 | 4.47 |
| Cadinene | (1S,4S,4αS,6R,8αR)-1,6-dimethyl-4-propan-2-yl-1,2,3,4,4α,5,6,8α-octahydronaphthalene | 880143-55-5 | 275 | 7.346 |
| Cedrol | (1S,2R,5S,7R,8R)-2,6,6,8-tetramethyltricyclo[5.3.1.0$^{1,5}$]undecan-8-ol | 77-53-2 | 291 | 4.53 |
| Cedryl Acetate | [(1S,2R,8R)-2,6,6,8-tetramethyl-8-tricyclo[5.3.1.0$^{1,5}$]undecanyl] acetate | — | 303 | 5.436 |
| Cedryl Methyl Ether | (3R,3aR,6S,7S,8aS)-6-methoxy-3,6,8,8-tetramethyloctahydro-1H-3a,7-methanoazulene | 67874-81-1 | 301.8 | 5.08 |
| 5-CYCLOHEXADECEN-1-ONE | (E)-cyclohexadec-5-en-1-one | 37609-25-9 | 331 | 5.17 |
| Cyclohexyl Salicylate | cyclohexyl 2-hydroxybenzoate | 25485-88-5 | 304 | 5.265 |
| Cyclamen Aldehyde | 2-methyl-3-(4-propan-2-ylphenyl)propanal | 103-95-7 | 270 | 3.68 |
| Dihydro Isojasmonate | methyl 2-hexyl-3-oxocyclopentane-1-carboxylate | 37172-53-5 | 300 | 3.009 |
| Diphenyl Methane | benzylbenzene | 101-81-5 | 262 | 4.059 |
| DIPHENYL OXIDE | phenoxybenzene | 101-84-8 | 267.8 | 4.03 |
| Ethylene Brassylate | 1,4-dioxacycloheptadecane-5,17-dione | 105-95-3 | 332 | 4.554 |
| ethyl laurate | ethyl dodecanoate | 106-33-2 | 264.4 | 5.81 |
| Ethyl Methyl Phenyl Glycidate | ethyl 3-methyl-3-phenyloxirane-2-carboxylate | 77-83-8 | 260 | 3.165 |
| Ethyl Undecylenate | ethyl undec-10-enoate | 692-86-4 | 264 | 4.888 |
| iso-Eugenol | 2-methoxy-4-[(E)-prop-1-enyl]phenol | 97-54-1 | 266 | 2.547 |
| Exaltolide | oxacyclohexadecan-2-one | 106-02-5 | 280 | 5.346 |
| Farnesol | (2E,6E)-3,7,11-trimethyldodeca-2,6,10-trien-1-ol | 4602-84-0 | 306.1 | 4.72 |
| Galaxolide | 4,6,6,7,8,8-hexamethyl-1,3,4,7-tetrahydrocyclopenta[g]isochromene | 1222-05-5 | 260 | 5.482 |
| Geranyl Anthranilate | [(2E)-3,7-dimethylocta-2,6-dienyl] 2-aminobenzoate | 67859-99-8 | 312 | 4.216 |
| Hexadecanolide | oxacycloheptadecan-2-one | 109-29-5 | 294 | 6.805 |
| HEXAROSE | [(2E)-3,7-dimethylocta-2,6-dienyl] hexadecanoate | 3681-73-0 | 333.3 | 10.75 |
| Hexyl Cinnamic Aldehyde | (2E)-2-benzylideneoctanal | 165184-98-5 | 305 | 5.473 |
| Hexyl Salicylate | hexyl 2-hydroxybenzoate | 6259-76-3 | 290 | 5.26 |
| Iso E Super Or Wood | 1-((2S,3S)-2,3,8,8-tetramethyl-1,2,3,4,5,6,7,8-octahydronaphthalen-2-yl)ethan-1-one | 54464-57-2 | 325.3 | 4.72 |
| Isolongifolanone | 1,1,5,5-tetramethylhexahydro-2H-2,4a-methanonaphthalen-8(5H)-one | 23787-90-8 | 323.2 | 4.09 |
| Lauryl alcohol, ≥98% | dodecan-1-ol | 112-53-8 | 269.8 | 5 |
| Linalyl Benzoate | 3,7-dimethylocta-1,6-dien-3-yl benzoate | 126-64-7 | 263 | 5.233 |
| Lyral | 4-(4-hydroxy-4-methylpentyl)cyclohex-3-ene-1-carbaldehyde | 31906-04-4 | 324 | 2.85 |

TABLE 4-continued

Examples of Third and Fourth Groups of PRMs

| Perfume Raw Material (PRM) Name | IUPAC Name | CAS No. | Boiling Point, BP (° C.) | ClogP |
|---|---|---|---|---|
| 2-Methoxy Naphthalene | 2-methoxynaphthalene | 93-04-9 | 275 | 3.235 |
| Methyl Cinnamate | methyl (E)-3-phenylprop-2-enoate | 103-26-4 | 263 | 2.62 |
| Methyl Dihydrojasmonate | methyl 2-[(1R,2R)-3-oxo-2-pentylcyclopentyl]acetate | 2630-39-9 | 300 | 2.275 |
| beta-Methyl Naphthyl ketone | 1-naphthalen-2-ylethanone | 93-08-3 | 300 | 2.275 |
| MAGNOLAN | 2,4-dimethyl-4,4α,5,9b-tetrahydroindeno[1,2-d][1,3]dioxine | 27606-09-3 | 340 | 2.99 |
| MAJANTOL | 2,2-dimethyl-3-(m-tolyl)propan-1-ol | 103694-68-4 | 281.3 | 3.04 |
| Musk Ketone | 1-(4-tert-butyl-2,6-dimethyl-3,5-dinitrophenyl)ethanone | 81-14-1 | M.P.[1] = 137 | 3.014 |
| Musk Tibetine | 1-tert-butyl-3,4,5-trimethyl-2,6-dinitrobenzene | 145-39-1 | M.P. = 136 | 3.831 |
| Myristicin | 4-methoxy-6-prop-2-enyl-1,3-benzodioxole | 607-91-0 | 276 | 3.2 |
| delta-Nonalactone | 6-butyloxan-2-one | 3301-94-8 | 280 | 2.76 |
| Patchouli Alcohol | (1R,3R,6S,7S,8S)-2,2,6,8-tetramethyltricyclo[5.3.1.0$^{3,8}$]undecan-3-ol | 5986-55-0 | 285 | 4.53 |
| Phantolide | 1-(1,1,2,3,3,6-hexamethyl-2H-inden-5-yl)ethanone | 15323-35-0 | 288 | 5.977 |
| PHENYL HEXANOL | 3-methyl-5-phenylpentan-1-ol | 4471-05-0 | 287.0 | 2.96 |
| Thibetolide | oxacyclohexadecan-2-one | 106-02-5 | 280 | 6.246 |
| delta-Undecalactone | 6-hexyloxan-2-one | 710-04-3 | 290 | 3.83 |
| gamma-Undecalactone | 5-heptyloxolan-2-one | 104-67-6 | 297 | 4.14 |
| Vanillin | 4-hydroxy-3-methoxybenzaldehyde | 121-33-5 | 285 | 1.58 |
| Vetiveryl Acetate | (4,8-dimethyl-2-propan-2-ylidene-3,3α,4,5,6,8α-hexahydro-1H-azulen-6-yl) acetate | 117-98-6 | 285 | 4.882 |
| Yara-Yara | 2-methoxynaphthalene | 93-04-9 | 274 | 3.235 |

Wherein the value of a+b is from 5 to 10, the perfume may comprise at least 80, preferably 80 to 10000, more preferably from 8500 to 1000%, even more preferably from 90% to 1000, by weight of the perfume of perfume raw materials having an CogP greater than 2.0, preferably at least 2.5, more preferably greater than 3.0, even more preferably greater than 3.5; preferably the weighted average C log P for the perfume is from 2.5 to 6.0, more preferably from 3.5 to 6.0.

Further, wherein the value of e+f is from 5 to 10, the perfume may comprise at least 80, preferably 80 to 1000%, more preferably from 85% to 1000%, even more preferably from 90% to 1000, by weight of the perfume of perfume raw materials having an CogP greater than 2.0, preferably at least 2.5, more preferably greater than 3.0, even more preferably greater than 3.5; preferably the weighted average C log P for the perfume is from 2.5 to 6.0, more preferably from 3.5 to 6.0.

The total weight ratio of the alkoxylated aromatic to the perfume may be 0.01:1 to 20,000:1, preferably 0.1:1 to 500:1, more preferably 0.15:1 to 100:1, even more preferably 0.15:1 to 20:1. Perfume raw materials which may be used include, but are not limited to, exemplary perfume raw materials as shown in Table 5 below.

TABLE 5

| Perfume Raw Material (PRM) | CAS | ClogP |
|---|---|---|
| Ligustral Or Triplal | 68039-49-6 | 2.98 |
| Citronellol | 106-22-9 | 3.56 |
| HYDROXYCITRONELLAL | 107-75-5 | 2.08 |
| Linalool | 78-70-6 | 3.29 |
| Methyl Phenyl Carbinyl Acetate | 93-92-5 | 2.38 |
| Pyranol | 63500-71-0 | 2.31 |
| Ethyl Maltol | 4940-11-8 | 0.5 |
| Ethyl Vanillin | 121-32-4 | 1.59 |
| Benzyl acetate | 140-11-4 | 1.94 |
| Helional | 1205-17-0 | 2.03 |
| Cyclo Galbanate | 68901-15-5 | 2.88 |
| 4-tertiary-Butyl cyclohexyl acetate | 32210-23-4 | 4.46 |
| Verdox | 88-41-5 | 4.46 |
| Orange Terpenes | 68647-72-3 | 4.15 |
| UNDECALACTONE | 104-67-6 | 3.18 |
| LINALYL ACETATE | 115-95-7 | 3.92 |
| Hexyl salicylate | 6259-76-3 | 4.85 |
| Habanolide 100% | 111879-80-2 | 4.77 |
| Iso E super | 54464-57-2 | 4.72 |
| Ionone Gamma Methyl | 127-51-5 | 4.22 |
| Ethyl Trimethylcyclopenteene Butenol | 28219-61-6 | 4.38 |

D. Sulfur-Containing Pro-Perfume

The freshening composition may comprise a sulfur-containing pro-perfume. A technical effect of the sulfur-containing pro-perfume is that it improves the stability of freshening compositions. The sulfur-containing pro-perfume compound may be present at various levels in the composition. Specifically, the freshening composition may comprise from about 0.001% to about 5%, alternatively from about 0.001% to about 3%, alternatively from about 0.01% to about 1%, alternatively about 0.01% to about 0.5%, alternatively about 0.01% to about 0.1%, alternatively at least about 0.02%, alternatively at least about 0.02%, or different combinations of the upper and lower percentages described above or combinations of any integer in the ranges listed above of a sulfur-containing pro-perfume by weight of the freshening composition.

The sulfur-containing pro-perfume herein may comprise a compound 5 of formula (I):

   (I)

wherein:
(i) Y is a radical selected from the group consisting of (Y-1) to (Y-7) shown herein below, including isomeric forms:

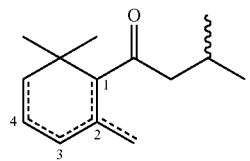 (Y-1)

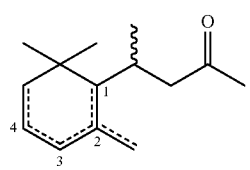 (Y-2)

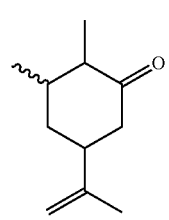 (Y-3)

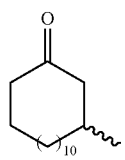 (Y-4)

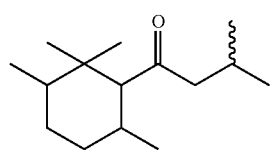 (Y-5)

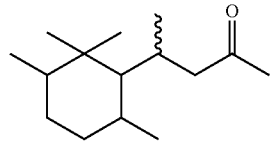 (Y-6)

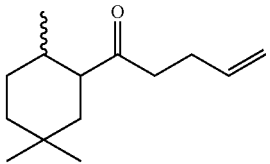 (Y-7)

wherein the wavy lines represent the location of the sulfur (S) bond, and the dotted lines represent a single or double bond;
(ii) G is selected from a divalent or trivalent radical derived from a linear or branched alkyl or alkenyl radical having from 2 to 15 carbon atoms; and (iii) Q is selected from a hydrogen, a —S—Y group, or a —NR$^2$—Y group, wherein Y is independently selected as defined above, and R2 is selected from a hydrogen or a C1-C3 alkyl group, G, may be a divalent or trivalent radical, preferably a divalent radical derived from a linear or branched alkyl or alkenyl radical having from 2 to 15 carbon atoms, substituted with one or more groups selected from the group consisting of —OR$^1$, —NR$^{12}$, —COOR$^1$, R$^1$ groups, and a combination thereof, wherein R$^1$ is selected from a hydrogen or a C$_1$ to C$_6$ alkyl or alkenyl group.

Preferably, G is a divalent radical derived from a linear or branched alkyl or alkenyl radical having from 2 to 15 carbon atoms, substituted with at least one —COOR$^1$ group, preferably substituted with a —COOR$^1$ group, wherein R$^1$ is selected from a hydrogen or a C$_1$ to C$_6$ alkyl or alkenyl group. Even more preferably, G is a divalent radical derived from a linear alkyl radical having a —CH2CH(COOR$^1$) group, wherein R$^1$ is a hydrogen or a methyl or ethyl group. G may be a divalent radical derived from a linear alkyl radical having from 8 to 15 carbon atoms which is either substituted or un-substituted.

The sulfur-containing pro-perfume may be a compound of formula (I) wherein Y is selected from Y-1, Y-2 or Y-3 groups as defined above, and G and Q are defined in any one of the above-described examples. The sulfur-containing pro-perfume may be a sulfide.

Preferably, the sulfur-containing pro-perfume is selected from the group consisting of methyl or ethyl 2-(4-oxo-4-(2,6,6-trimethylcyclohex-3-en-1-yl)butan-2-ylamino)-3-(4-oxo-4-(2,6,6-trimethylcyclohex-3-en-1-yl)butan-2-ylthio) propanate, methyl or ethyl 2-(4-oxo-4-(2,6,6-trimethylcyclohex-2-en-1-yl)butan-2-ylamino)-3-(4-oxo-4-(2,6,6-trimethylcyclohex-2-en-lyl)butan-2-ylthio)propanate, methyl or ethyl 2-(2-oxo-4-(2,6,6-trimethylcyclohex-1-en-1-yl)butan-4-ylamino)-3-(2-oxo-4-(2,6,6-trimethylcyclohex-1-en-1-yl)butan-4-ylthio)propanate, methyl or ethyl 2-(2-oxo-4-(2,6,6-trimethylcyclohex-2-en-1-yl)butan-4-ylamino)-3-(2-oxo-4-(2,6,6-trimethylcyclohex-2-en-1-yl)butan-4-ylthio)propanate, 3-(dodecylthio)-1-(2,6,6-trimethylcyclohex-3-en-1-yl)-1-butanone, 3-(dodecylthio)-1-(2,6,6-trimethylcycloh ex-2-en-1-yl)-lbutanone,4-(dodecylthio)-4-(2,6,6-trimethylcyclohex-2-en-1-yl)-2-butanone, 4-(dodecylthio)-4-(2,6,6-trimethylcyclohex-1-en-1-yl)-2-butanone, 2-dodecylsulfanyl-5-methyl-heptan-4-one, 2-cyclohexyl-1-dodecylsulfanyl-hept-6-en-3-one, 3-(dodecylthio)-5-isopropenyl-2-methylcyclohexanone, and a combination thereof. More preferably, the sulfur-containing pro-perfume compound is selected from the group consisting of 3-(dodecylthio)-1-(2,6,6-trimethylcyclohex-3-en-1-yl)-1-butanone, 4-(dodecylthio)-4-(2,6,6-trimethylcyclohex-2-enl-yl)-2-butanone, 4-(dodecylthio)-4-(2,6,6-trimethylcyclohex-len-1-yl)-2-butanone and 3-(dodecylthio)-5-isopropenyl-2-methylcyclohexanone, and a combination thereof. 3-(dodecylthio)-1-(2,6,6-trimethylcyclohex-3-en-1-yl)-1-butanone is the most preferred sulfur-containing pro-perfume compound, such as Haloscent® D available from Firmenich located in Geneva, Switzerland, and is defined by its CAS No. 543724-31-8 and has a C log P of 9.51.

The freshening composition may comprise dodecyl thiodamascone having the general structure shown below.

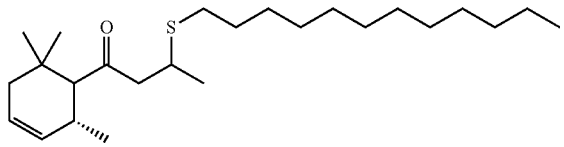 [SMILES: CCCCCCCCCCCCSC(C)CC(=O)C1[C@H](C)C=CCC1(C)C]

Thio-damascone may be present in an amount from about 0.01% to about 1.0%, alternatively from about 0.001% to about 5.0%, alternatively from about 0.001% to about 3.0%, alternatively from about 0.01% to about 1.0%, alternatively about 0.01% to about 0.5%, alternatively about 0.01% to about 0.1%, alternatively at least about 0.02%, alternatively at least about 0.02%, by weight of the freshening composition.

The weight ratio of perfume mixture to sulfur-containing pro-perfume may be about 0.01:1 to about 200:1, or about 5:1 to about 50:1, or about 10:1 to about 40:1, or about 10:1 to about 20:1, by weight of the composition.

E. Solvents

The freshening composition may comprise a solvent for solubilizing the perfume. Specifically, the composition may comprise less than 10%, from 0.01% to 5%, from 0.01% to 3%, from 0.01% to 1%, from 0.01% to 0.05%, or different combinations of the upper and lower percentages described above or combinations of any integer in the ranges listed above of a solvent by weight of the freshening composition. The solvent may be selected from a group consisting of: an alcohol, a polyol and mixtures thereof. The solvent may comprise low molecular weight monohydric alcohols (e.g., ethanol, methanol, and isopropanol, or polyols, such as ethylene glycol and propylene glycol).

When the freshening composition is formulated with ethanol together with alkoxylated aromatic to define a solvent system, ethanol may be in an amount of less than 10%, preferably less than 5%, even more preferably less than 3%, yet even more preferably from 0.1% to 2% by weight of the freshening composition. Preferably the alkoxylated aromatic is an ethoxylated aromatic.

The freshening composition may be substantially free of a solvent, preferably free of alcohol, more preferably free of ethanol, even more preferably free of a polyol selected from the group consisting of: dipropylene glycol methyl ether, diethylene glycol, 3-methoxy-3-methyl-1-butanol, and mixtures thereof, yet even more preferably free of diethylene glycol.

F. Surfactants

The freshening composition may contain a surfactant to solubilize any excess hydrophobic organic materials, particularly any PRMs, and also optional ingredients (e.g., insect repelling agent, antioxidant, etc.) which can be added to the composition, that are not readily soluble in the composition, to form a clear solution. The freshening composition may comprise less than 3.5%, from 0.01% to 3%, from 0.01% to 1%, from 0.01% to 0.05% of a surfactant by weight of the freshening composition. A suitable surfactant is a no-foaming or low-foaming surfactant. The surfactant may be selected from the group consisting of: nonionic surfactants, cationic surfactants, amphoteric surfactants, zwitterionic surfactants and mixtures thereof. Non-ionic surfactants may further include polyoxy-ethylene castor oil ethers or polyoxyethylene hardened castor oil ethers or mixtures thereof, which are either partially or fully hydrogenated. These ethoxylates have the following formula:

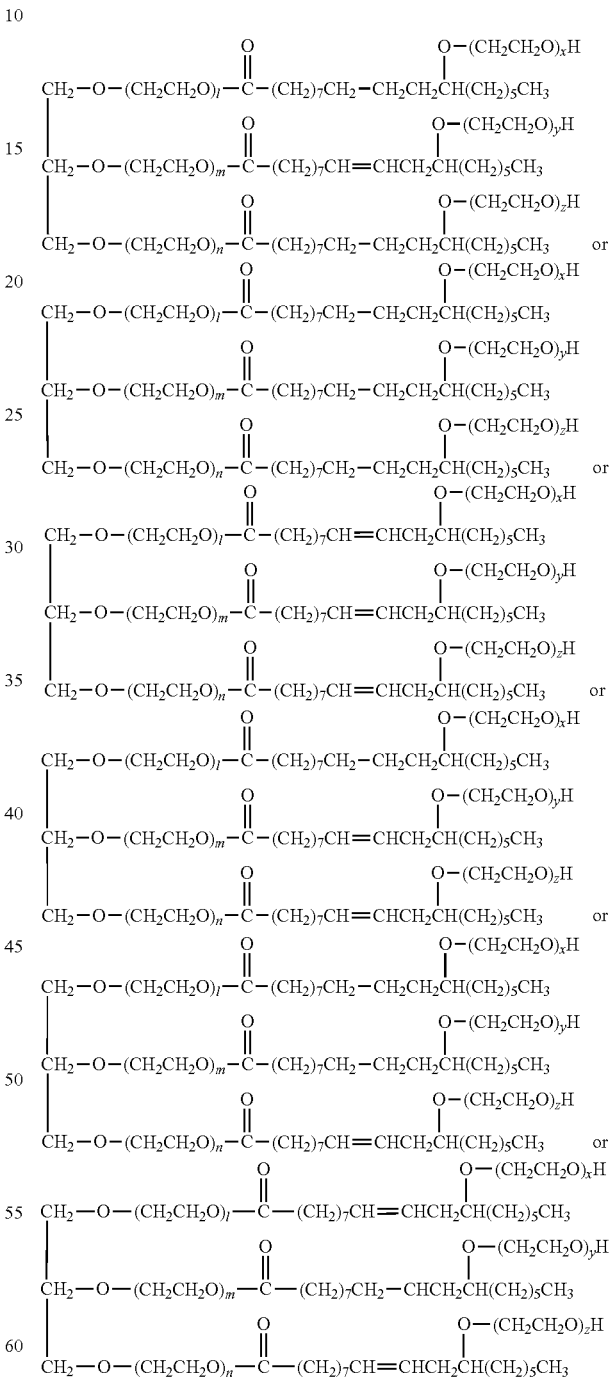

These ethoxylates can be used alone or in any mixture thereof. The average ethylene oxide addition mole number (i.e., $1+m+n+x+y+z$ in the above formula) of these ethoxylates is generally from about 7 to about 100, from about 20 to about 80, or different combinations of the upper and lower integers described above or combination of any integer n the ranges listed above.

Exemplary nonionic surfactants may include castor oil surfactants commercially available from Nikko under tradenames HCO 40 and HCO60, from BASF under the tradenames Cremophor RH40, RH60 and CO60, Basophor ELH60, from The Dow Chemical Company under the tradenames Tergitol™ ECO-20, Tergitol™ ECO-36 and Tergitol™ECO-40.

Further examples of nonionic surfactants may include condensates of from 3 to 30 moles of ethylene oxide with an aliphatic alcohol of 8 to 22 carbon atoms, condensates of 5 to 30 moles of ethylene oxide with an alkyl phenol wherein the alkyl contains 9 to 15 carbon atoms and $C_8$ to $C_{22}$ alkyl dimethyl amine oxides. An exemplary nonionic surfactant may be a secondary alcohol ethoxylate known as Tergitol™ 15-, available from The Dow Chemical Company.

Examples of ampholytic and zwitterionic surfactants are found in U.S. Pat. No. 3,929,678, Laughlin et al., issued Dec. 30, 1975 at Col, 19, line 38 through Col. 22 line 48. Examples of cationic surfactants are tetraalkyl quaternary ammonium salts having at least one alkyl chain of 8 to 22 carbon atoms, wherein the other alkyl groups can contain from 1 to 22 carbon atoms and wherein the anionic counterion is halogen ethylsulfate or methylsulfate.

G. Malodor Binding Polymer

The freshening composition of the present invention may comprise a malodor binding polymer. A malodor binding polymer is polymer having an available functional group (e.g. amine) that has the affinity to neutralize malodor components. Monomers having an available function group with an affinity to neutralize malodor components are also contemplated. In the case of amine based compounds, the amine will have an affinity for aldehyde malodors. The amine may react with aldehyde malodors and form a new compound, such as an aminol, imine, or enamine which is not odorous.

A malodor binding polymer may include amine based compounds, such as monoamines, amino acids, polyethyleneimine polymers (PEIs), modified PEIs, substituted PEIs; acrylic acid polymers, such as polyacrylate co-polymer (e.g. Acumer™ 9000 from Rohm & Haas), polyacrylic acid polymers (e.g. Acusol™ from Rohm & Haas), and modified acrylate copolymers (e.g. Aculyn™ from Rohm & Haas); and modified methacrylate copolymers (e.g. HydroSal™ from Salvona Technologies); or mixtures thereof.

1. Amine Based Compounds

The malodor binding polymer may be an amine based compound with a molecular weight greater than 100 Daltons and at least 10% of its amine groups are primary amines. The amine-based compound may be a polyamine with a molecular weight greater than 150 Daltons and 15% to 80% of its amine groups are primary amines. The malodor binding polymer may be an amine-based compound with a molecular weight greater than 1000 Daltons and from 0% to about 10% or less than 10% of its amine groups are primary amines.

A general structure for a primary amine compound useful in this invention is as follows:

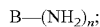

wherein B is a carrier material, and n is an index of value of at least 1. Suitable B carriers include both inorganic and organic carrier moieties. By "inorganic carrier", it is meant a carrier which is comprised of non- or substantially noncarbon based backbones.

Compounds containing a secondary amine group have a structure similar to the above with the exception that the compound comprises one or more —NH— groups as well as —NH2 groups. The amine compounds of this general type may be relatively viscous materials.

Exemplary amine based compounds are those selected from monoamines, aminoaryl derivatives, polyamines and derivatives thereof, polyamino acids and copolymers thereof, glucamines, dendrimers, PEIs, substituted amines and amides monoamines, or mixtures thereof.

a. Monoamines

Monoamines may be utilized in the present invention. Nonlimiting examples of suitable monoamines for use in the present invention include, but are not limited to, primary amines that also contain hydroxy and/or alkoxy functional groups, such as the 2-hydroxyamines and/or 3-hydroxyamines; primary or secondary amines that also contain a functional group that enhances deposition of the monoamine compared to monoamines that lack that functional group, especially when the monoamine is interacting with the benefit agent. Primary monoamines may also be used herein in combination with secondary monoamines. However, sufficient levels of the primary monoamine must be used to provide at least 10% of the total amine groups within such combinations as primary amine groups.

b. Aminoaryl Derivatives

Exemplary aminoaryl derivatives are the amino-benzene derivatives including the alkyl esters of 4-amino benzoate compounds, ethyl-4-amino benzoate, phenylethyl-4-aminobenzoate, phenyl-4-aminobenzoate, 4-amino-N'-(3-aminopropyl)-benzamide, or mixtures thereof.

c. Polyamines

Examples of suitable amino functional polymers containing at least one primary amine group for the purposes of the present invention are: Polyvinylamine with a MW of 300-2.10E6 Daltons (e.g Lupamine series 1500, 4500, 5000, 9000 available from BASF); Polyvinylamine alkoxylated with a MW of ≥600 Daltons and a degree of ethoxylation of at least 0.5; Polyvinylamine vinylalcohol-molar ratio 2:1, polyvinylaminevinylformamide-molar ratio 1:2 and polyvinylamine vinylformamide-molar ratio 2:1; Triethylenetetramine, diethylenetriamine, tetraethylenepentamine; Bisaminopropylpiperazine; amino substituted polyvinylalcohol with a MW ranging from 400-300,000 Daltons; polyoxyethylene bis[amine] available from e.g. Sigma; polyoxyethylene bis[6-aminohexyl] available from e.g. Sigma; N,N'-bis-(3-aminopropyl)-1,3-propanediamine linear or branched (TPTA); N,N'-bis-(3-aminopropyl)ethylenediamine; bis (amino alkyl)alkyl diamine, linear or branched; and 1,4-bis-(3-aminopropyl)piperazine (BNPP).

d. Polyamino Acids

Suitable amine based compounds include polyamino acids. Polyamino acids are made up of amino acids or chemically modified amino acids. The amino acids may be selected from cysteine, histidine, isoleucine, tyrosine, tryptophane, leucine, lysine, glutamic acid, glutamine, glycine, alanine, aspartic acid, arginine, asparagine, phenylalanine, proline, serine, histidine, threonine, methionine, valine, and mixtures thereof. Amino acid derivatives may be tyrosine ethylate, glycine methylate, tryptophane ethylate, or mixtures thereof; homopolymers of amino acids; hydroxyamines; polyamino acids; or mixtures thereof.

In chemically modified amino acids, the amine or acidic function of the amino acid has reacted with a chemical reagent. This is often done to protect these chemical amine and acid functions of the amino acid in a subsequent reaction or to give special properties to the amino acids, like improved solubility. Examples of such chemical modifications are benzyloxycarbonyl, aminobutyric acid, butyl ester, and pyroglutamic acid. More examples of common modifications of amino acids and small amino acid fragments can be found in the Bachem, 1996, Peptides and Biochemicals Catalog.

One polyamino acid is polylysine, alternatively polylysines or polyamino acids where more than 50% of the amino acids are lysine, since the primary amine function in the side chain of the lysine is the most reactive amine of all amino acids. One polyamino acid has a molecular weight of 500 to 10,000,000, alternatively between 2000 and 25,000.

The polyamino acid can be cross linked. The cross linking can be obtained for example by condensation of the amine group in the side chain of the amino acid like lysine with the carboxyl function on the amino acid or with protein cross linkers like PEG derivatives. The cross linked polyamino acids still need to have free primary and/or secondary amino groups left for neutralization. Cross linked polyamino acid has a molecular weight of 20,000 to 10,000,000; alternatively between 200,000 and 2,000,000.

The polyamino acid or the amino acid can be co-polymerized with other reagents like for instance with acids, amides, acyl chlorides, aminocaproic acid, adipic acid, ethylhexanoic acid, caprolactam, or mixtures thereof. The molar ratio used in these copolymers ranges from 1:1 (reagent/amino acid (lysine)) to 1:20, alternatively from 1:1 to 1:10. The polyamino acid like polylysine can be unethoxylated or partially ethoxylated so long as the requisite amount of primary amine remains in the polymer.

e. Dendrimers

Also useful amine based compounds are polypropylenimine dendrimers and the commercially available Starburst® polyamidoamines (PAMAM) dendrimers, generation G0-G10 from Dendritech and the dendrimers Astromols®, generation 1-5 from DSM being DiAminoButane PolyAmine DAB (PA)x dendrimers with x=2<n>×4 and n being generally comprised between 0 and 4.

f. PEIs

In one embodiment, the malodor binding polymer is a PEI. It has been surprisingly discovered that amine based polymers at a pH of about 4 to about 8, alternatively above 5 to about 8, alternatively 7 can neutralize amine based odors. PEIs have the following general formula:

—(CH2-CH2-NH)$_n$—;n=10-10$_5$

Homopolymeric PEIs are branched, spherical polyamines with a well defined ratio of primary, secondary and tertiary amine functions. They are best described in the following partial structural formula:

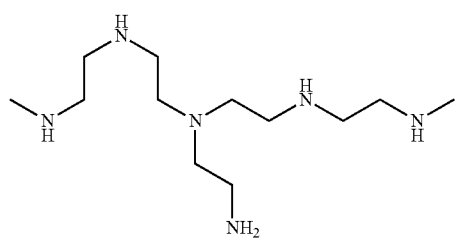

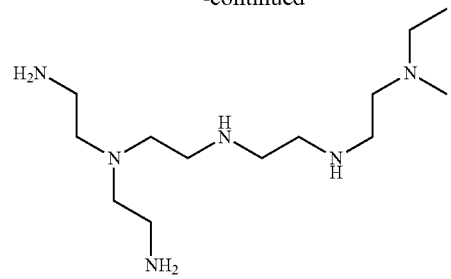

The chemical structure of homopolymeric PEIs follows a simple principle: one amine function—two carbons.

The freshening composition may comprise a homopolymeric polyethylenimine having a molecular weight of about 800 to about 2,000,000, alternatively about 1,000 to about 2,000,000, alternatively about 1,200 to about 25,000, alternatively about 1,300 to about 25,000, alternatively about 2,000 to about 25,000, alternatively about 10,000 to about 2,000,000, alternatively about 25,000 to about 2,000,000, alternatively about 25,000. Exemplary homopolymeric PEIs include those that are commercially available under the tradename Lupasol® from BASF. Lupasol products are usually obtained through polymerization of the ethylenimine monomer. The ethylenimine monomer has totally reacted in the polymer matrix. Suitable Lupasol products include Lupasol FG (MW 800), G20wfv (MW 1300), PR8515 (MW 2000), WF (MW 25,000), FC (MW 800), G20 (MW 1300), G35 (MW 1200), G100 (MW 2000), HF (MW 25,000), P (MW 750,000), PS (MW 750,000), SK (MW 2,000,000), SNA (MW 1,000,000).

The freshening composition may comprise Lupasol HF or WF (MW 25,000), P (MW 750,000), PS (MW 750,000), SK (MW 2,000,000), G20wfv (MW 1300) or PR 1815 (MW 2000), or Epomin SP-103, Epomin SP-110, Epomin SP-003, Epomin SP-006, Epomin SP-012, Epomin SP-018, Epomin SP-200, or partially alkoxylated polyethyleneimine, like polyethyleneimine 80% ethoxylated from Aldrich. The freshening composition may comprise Lupasol WF (MW 25,000).

Also suitable amine based compounds for use in the freshening composition are modified PEIs, partially alkylated polyethylene polymers, PEIs with hydroxyl groups, 1,5-pentanediamine, 1,6-hexanediamine, 1,3 pentanediamine, 3-dimethylpropanediamine, 1,2-cyclohexanediamine, 1,3-bis(aminomethyl)cyclohexane, tripropylenetetraamine, bis(3-aminopropyl)piperazine, dipropylenetriamine, tris(2-aminoethylamine), tetraethylenepentamine, bishexamethylenetriamine, bis(3-aminopropyl) 1,6-hexamethylenediamine, 3,3'-diamino-N-methyldipropylamine, 2-methyl-1,5-pentanediamine, N,N,N',N'-tetra(2-aminoethyl)ethylenediamine, N,N,N',N'-tetra(3-aminopropyl)-1,4-butanediamine, pentaethylhexamine, 1,3-diamino-2-propyl-tert-butylether, isophorondiamine, 4,4',-diaminodicyclohylmethane, N-methyl-N-(3-aminopropyl)ethanolamine, spermine, spermidine, 1-piperazineethaneamine, 2-(bis(2-aminoethyl)amino)ethanol, ethoxylated N-(tallowalkyl)trimethylene diamines,poly[oxy(methyl-1,2-ethanediyl)], α-(2-aminomethyl-ethoxy)-(=C.A.S No. 9046-10-0); poly[oxy(methyl-1,2-ethanediyl)], α-hydro-)-ω-(2-aminomethylethoxy)-, ether with 2-ethyl-2-(hydroxymethyl)-1,3-propanediol (=C.A.S. No. 39423-51-3); commercially available under the tradename Jeffamines T-403, D-230, D-400, D-2000; 2,2',2"-triaminotriethylamine; 2,2'-diamino-diethylamine; 3,3'-diamino-dipropylamine, 1,3 bis aminoethyl-cyclohexane commercially available from Mitsubishi, and the C12 Sternamines commercially available from Clariant like the C12 Sternamin(propylenamine)n with n=3/4.

Suitable levels of malodor binding polymer are from about 0.01% to about 2%, alternatively from about 0.01% to about 1%, alternatively about 0.01% to about 0.8%, alternatively about 0.01% to about 0.6%, alternatively about 0.01% to about 0.1%, alternatively about 0.01% to about 0.07%, alternatively about 0.07%, by weight of the freshening composition. Compositions with higher amount of malodor binding polymer may make fabrics susceptible to soiling and/or leave unacceptable visible stains on fabrics as the solution evaporates off of the fabric.

H. Malodor Counteractant

The freshening composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces. For example, aliphatic aldehydes react with amine odors, such as fish and cigarette odors. When used in combination with the malodor binding polymer, the freshening composition may neutralize a broader range of malodor causing materials which, in turn, further reduces malodors in the air or on inanimate surfaces.

Specifically, the freshening composition may include a malodor counteractant, wherein the malodor counteractant is selected from the group consisting of: polyols, cyclodextrin and derivatives thereof, amine functional polymers, aldehydes, and combinations thereof. The malodor counteract may be cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

I. Buffering System

The freshening composition may include a buffering agent. The buffering agent may be an acidic buffering agent. The buffering agent may be a dibasic acid, carboxylic acid, dicarboxylic acid such as maleic acid, tricarboxylic acid such as citric acid, or a polycarboxylic acid such as polyacrylic acid. The carboxylic acid may be, for example, citric acid, polyacrylic acid, or maleic acid. The acid may be sterically stable. The acid may be used in the composition for maintaining the desired pH. The freshening composition may have a pH from about 4 to about 9, alternatively from about 4 to about 8.5, alternatively from about 4 to about 6.9, alternatively about 4 to about 6.7. Preferably, the buffer system comprises one or more buffering agents selected from the group consisting of: citric acid, maleic acid, polyacrylic acid, and combinations thereof. It has been found that buffer systems that include a buffering agent selected from the group consisting of: citric acid, maleic acid, polyacrylic acid, and combinations thereof provide stable freshening compositions with prolonged shelf life.

Preferably, the buffer system comprises citric acid and sodium citrate. It has been found that buffer systems comprising citric acid and sodium citrate provide stable freshening compositions with a prolonged shelf life. Other suitable buffering agents for the freshening compositions include biological buffering agents. Some examples are nitrogen-containing materials, sulfonic acid buffers like 3-(N15489 morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine or methyldiethanolamine or derivatives thereof. Other nitrogen containing buffering agents are tri(hydroxymethyl)amino methane (HOCH2)5 3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetramethyl-1,3-diamino-2-propanol, N,N-bis(2-hydroxyethyl) glycine (bicine) and N-tris (hydroxymethyl)methyl glycine (tricine). Mixtures of any of the above are also acceptable.

The freshening compositions may include a secondary or tertiary amine. The freshening compositions may contain at least about 0%, alternatively at least about 0.0001%, alternatively at least about 0.01%, by weight of the composition, of a buffering agent. The composition may also contain no more than about 2%, alternatively no more than about 0.75%, alternatively no more than about 0.5%, by weight of the composition, of a buffering agent.

J. Wetting Agent

The freshening composition may, optionally, include a wetting agent that provides a low surface tension that permits the composition to spread readily and more uniformly on hydrophobic surfaces like polyester and nylon. It has been found that the freshening composition, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated freshening compositions. Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic™ and Tetronic™ by the BASF-Wyandotte Corp., Wyandotte, Michigan, are readily available.

Non-limiting examples of cyclodextrin-compatible wetting agents of this type are described in U.S. Pat. No. 5,714,137 and include the SILWET™ surfactants available from Momentive Performance Chemical, Albany, New York Exemplary SILWET™ surfactants are as follows in Table 6 below. However, it will be appreciated that mixtures of the following surfactants may also be used in the present invention.

TABLE 6

| SILWET ™ Surfactants | Average MW |
| --- | --- |
| L-7608 | 600 |
| L-7607 | 1,000 |

TABLE 6-continued

| SILWET ™ Surfactants | Average MW |
|---|---|
| L-77 | 600 |
| L-7605 | 6,000 |
| L-7604 | 4,000 |
| L-7600 | 4,000 |
| L-7657 | 5,000 |

The total amount of surfactants e.g. solubilizer, wetting agent in the freshening composition is from 0 wt. % to about 3 wt. % or no more than 3 wt. %, alternatively from 0 wt. 5% to about 1 wt. % or no more than 1 wt. %, alternatively from 0 wt. % to about 0.9 wt. % or no more than 0.9 wt. %, alternatively from 0 wt. % to about 0.7 wt. % or no more than 0.7 wt. %, alternatively from 0 wt. % to about 0.5 wt. % or no more than 0.5 wt. %, alternatively from 0 wt. % to 0.3 wt. % or no more than about 0.3 wt. %, by weight of the composition. Compositions with higher concentrations can make fabrics susceptible to soiling and/or leave unacceptable visible stains on fabrics as the solution evaporates. The weight ratio of sulfur-containing pro-perfume to total surfactant may be from about 1:1 to about 1:250, or from about 1:1 to about 1:60, or from about 1:1 to about 1:30.

II. Method of Manufacture

The freshening composition can be made in any suitable manner known in the art. All of the ingredients can simply be mixed together. In certain embodiments, it may be desirable to make a concentrated mixture of ingredients such as a pre-mix and dilute by adding the same to an aqueous carrier before dispersing the composition into the air or on an inanimate surface. A method of manufacturing a freshening composition may comprise the steps of:

i) mixing alkoxylated aromatic and perfume to form a pre-mix, wherein the weight ratio of the alkoxylated aromatic to the perfume is 0.01:1 to 100:1, preferably 0.1:1 to 10:1, even more preferably 0.15:1 to 1:1; and ii) adding the premix to the water to form the freshening composition.

In another embodiment, the ethoxylated aromatic may be dispersed in one vessel containing ingredients such as water and may contain additional ingredients such as ethanol, low molecular polyols, and buffer agents. All materials are added until fully dispersed and visually dissolved. In a separate vessel, the solubilizing materials (surfactants and solvents, and in some embodiments may contain the ethoxylated aromatic) and perfume are mixed until homogenous. The solution of solubilizing materials and perfume are then added to the first mixing vessel, and mixed until homogenous.

III. Method of Use

The freshening composition can be used by dispersing, e.g., by placing the freshening composition into a dispenser, such as a spray dispenser and spraying an effective amount into the air or onto the desired inanimate surface or article. "Effective amount", when used in connection with the amount of the freshening composition, means an amount sufficient to provide at least about 4 hours, or at least about 6 hours, or at least about 8 hours, or at least about 24 hours of freshness or scent to the treated air, surface, or article, yet not so much as to saturate or create a pool of liquid on an article or surface and so that, when dry, there is no visual deposit readily discernible. Where malodor reducing ingredients are included, "effective amount", when used in connection with the amount of the freshening composition, means an amount that provides the foregoing and also provides neutralization of a malodor to the point that it is not discernible by the human sense of smell, yet not so much as to saturate or create a pool of liquid on an article or surface and so that, when dry, there is no visual deposit readily discernible. Dispersing can be achieved by using a spray device, a roller, a pad, or other product forms described hereinafter.

Product Forms

Wipes

The freshening compositions of the present invention may be impregnated into a commercially available substrate such as the substrates discussed in U.S. RE38505, U.S. RE38105, and U.S. Pat. No. 6,936,330, all of which are incorporated herein by reference. In one embodiment, the substrate may be a non-woven, wet-wipe for deodorizing, disinfecting, or cleaning multiple surfaces including inanimate household surfaces.

Packaging Container

The freshening compositions of the present invention can be contained in plastic containers constructed of hydrophilic perfume compatible materials. These materials avoid complexing, with hydroplilic perfume ingredients, such that absorption by and/or transmission through plastic containers is minimized. Suitable hydrophilic perfume compatible materials can be readily identified by determining the average hydrophilic perfume loss through gas chromatography analysis. Hydrophilic perfume compatible materials result in an average hydrophilic perfume ingredient loss of less than about 50% alternatively less than about 20%, alternatively less than about 15% and alternatively less than about 10% of the originally present individual hydrophilic perfume ingredients.

Freshening compositions containing a substantial amount of hydrophilic perfume ingredients can be stored in plastic container constructed of at least 80% hydrophilic perfume compatible materials for 8 weeks at ambient temperature. After storage, gas chromatography analysis is used to determine the amount of the various perfume ingredients remaining in the aqueous composition and approximate loss is calculated based on the amount of each ingredient originally present.

An effective amount of hydrophilic perfume compatible materials suitable for the present invention is at least about 80%, alternatively about 80% to about 100%, alternatively about 90% to about 100%, and alternatively 100%, by weight of the container. Non-limiting examples of hydrophilic perfume compatible materials are any resins of high density polyethylene (HDPE), low density polyethylene (LDPE), polyvinyl chloride (PVC), polypropylene (PP), polystyrene (PS), polyethylene-co-vinyl alcohol (EVOH), fluorinated polymer such as Aclar®, acrylonitrile-methyl acrylate copolymer such as Barex®, or mixtures thereof. Alternatively HDPE is utilized in the present invention.

In one embodiment, an HDPE bottle, from Plastipak Packaging Inc. Champaign, Ill., is used to contain the aqueous composition of the present invention. HDPE bottles can be made by any blow molding, injection molding, and thermoform process known in the art. For example, for blow molded bottles, heat softened HDPE is extruded as a hollow tube into a mold cavity and forced by pressurized air against the walls of the cold mold cavity to form the bottle. The bottle solidifies by cooling.

It has been found that the perfume compositions having a C log P of less than about 3 are not fully absorbed into and/or transmitted through the hydrophilic perfume compatible materials such as PP and HDPE. Thus, this assists in preventing transmission of perfume ingredients through plastic containers; which in turn provides consumer noticeable longer lasting fragrance life. Any of the hydrophilic perfume compatible materials can be used in conjunction with one or more barrier materials including amorphous carbon, silicone oxide or mixtures thereof and metallized coating.

Freshening Product

The freshening composition can be packaged in any suitable package to form a freshening product. The package may be in the form of a spray dispenser and the freshening product may be a freshening sprayer product. The spray dispenser may be transparent or translucent such that the freshening composition is visible or at least partially visible from outside of the freshening product.

The spray dispenser may hold various amounts of freshening composition. The spray dispenser may be capable of withstanding internal pressure in the range of about 20 p.s.i.g. to about 140 psig, alternatively about 80 to about 130 p.s.i.g. The total composition output and the spray droplet/particle size distribution may be selected to support the particulate removal efficacy but avoid a surface wetness problem. Total output is determined by the flow rate of the composition as it is released from the spray dispenser. To achieve a spray profile that produces minimal surface wetness, it is desirable to have a low flow rate and small 5 spray droplets.

The flow rate of the composition being released from the spray dispenser may be from about 0.0001 grams/second (g/s) to about 2.5 grams/second. Alternatively, the flow rate may be from about 0.001 grams/second to about 2.5 grams/second, or about 0.01 grams/second to about 2.0 grams/second. For an aerosol sprayer, the flow rate is determined by measuring the rate of composition expelled by a spray dispenser for any 60 second period of use.

The Sauter Mean Diameter of the spray droplets may be in the range of from about 10 µm to about 100 µm, alternatively from about 20 µm to about 60 µm. At least some of the spray droplets are sufficiently small in size to be suspended in the air for at least about 10 minutes, and in some cases, for at least about 15 minutes, or at least about 30 minutes. Small particles can be efficiently created when the spray is dispensed in a wide cone angle. For a given nozzle component and delivery tube, cone angles can be modified by varying the insertion depth of the nozzle in the delivery tube. The cone angle may be greater than about 20 degrees, or greater than about 30 degrees, or greater than about 35 degrees, or greater than about 40 degrees, or greater than about 50 degrees.

The spray dispenser may be configured to spray the freshening composition at an angle that is between an angle that is parallel to the base of the container and an angle that is perpendicular thereto. The desired size of spray droplets can be delivered by other types of spray dispensers that are capable of being set to provide a narrow range of droplet size. Such other spray dispensers include, but are not limited to: foggers, ultrasonic nebulizers, electrostatic sprayers, and spinning disk sprayers. The spray dispenser may be comprised of various materials, including plastic, metal, glass, or combinations thereof. The spray dispenser may be pressurized, unpressurized or non-aerosol.

A non-aerosol spray dispenser may include a pre-compression trigger sprayer.

One suitable non-aerosol spray dispenser is a plastic non-aerosol dispenser. The dispenser may be constructed of polyethylene such as a high-density polyethylene; polypropylene; polyethyleneterephthalate ("PET"); vinyl acetate, rubber elastomer, and combinations thereof. The spray dispenser may be made of clear PET. Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition. An example of the FLAIROSOL™ dispenser is described in U.S. Pat. No. 8,905,271B2.

A pressurized spray dispenser may include a propellant. Various propellants may be used. The propellant may comprise hydrocarbon(s); compressed gas(es), such as nitrogen, carbon dioxide, air; liquefied gas(es) or hydrofluoro olefin ("HFO"); and mixtures thereof. Preferably, the product comprises a propellant selected from the group consisting of compressed gas such as compressed air, compressed nitrogen, and combinations thereof. Propellants listed in the U.S. Federal Register 30 49 C.F.R. § 1.73.115, Class 2, Division 2.2 are considered acceptable. The propellant may particularly comprise a trans-1,3,3,3-tetrafluoroprop-1-ene, and optionally a CAS number 1645-83-6 gas. Such propellants provide the benefit that they are not flammable, although the freshening compositions are not limited to inflammable propellants. One such propellant is commercially available from Honeywell International of Morristown, New Jersey under the trade name HFO-5 1234ze or GWP-6. If desired, the propellant may be condensable. By "condensable", it is meant that the propellant transforms from a gaseous state of matter to a liquid state of matter in the spray dispenser and under the pressures encountered in use. Generally, the highest pressure occurs after the spray dispenser is charged with a freshening composition but before that first dispensing of that freshening composition by the user. A condensable propellant provides the benefit of a flatter depressurization curve as the freshening composition is depleted during usage.

The pressurized spray dispenser may be free of a hydrocarbon propellant. The freshening composition may be delivered from the spray dispenser which includes delivery components including but not limited to a valve to control flow and to seal the freshening composition within the spray dispenser, a button actuator and a nozzle for dispensing the freshening composition to the environment. The freshening composition may be contained in a bag-in-can plastic spray dispenser.

The following examples are intended to more fully illustrate the present invention and are not to be construed as limitations of the present invention since any variations thereof are possible without departing from the scope of the present invention. All parts, percentages and ratios used herein are expressed as percent weight unless otherwise specified.

Examples

Test equipment/materials and perfume compositions are first described under Materials, then Test Methods are provided, and lastly results are discussed. Equipment and materials for making the freshening compositions used in the Test Methods described hereinafter are listed in Table 7 and Table 8 below.

TABLE 7

Equipment/Materials

| Component (Ingredient) | Example | CAS | Commercial Name |
|---|---|---|---|
| Aqueous Carrier | Water | 7732-18-5 | Water |
| Solvent for PRM | Ethanol | 64-17-5 | Ethanol |
| Alkoxylated Aromatic for PRM | See Table 1 | — | — |
| Malodor Counteractant Polymer | Polyethyleneimine | 9002-98-6 | Lupasol HF |
| Solvent for Malodor Counteractant Polymer | Diethylene Glycol | 111-46-6 | Diethylene Glycol |
| Wetting Agent/Spreading Polymer | Polyalkyleneoxide Modified Polydimethylsiloxane | 68938-54-5 | Silwet L7600 |
| Wetting Agent/Spreading Material Surfactant | Didecyl dimethylammoium chloride | 7173-51-5 | Uniquat 2250 |
| Buffering Agent | Maleic Acid | 110-16-7 | Maleic Acid |
| Preservative | Benzisothiazolinone | 2634-33-5 | Koralone B-119 |
| Buffering Agent | Citric Acid | 77-92-9 | Citric Acid |
| Buffering Agent | Sodium Citrate | 6132-04-3 | Sodium Citrate |
| Perfume | Perfume Compositions 1, 2, 3 as detailed in Table | Not provided by manufacturer | Not provided by manufacturer |
| Surfactant | Hydrogenated, Ethoxylated Castor Oil | 61788-85-0 | Basophor ELH 60 |
| Surfactant | Ethoxylated Castor Oil | 61791-12-6 | Tergitol ECOsurf 36 |
| Surfactant | Dioctyl Sodium Sulfosuccinate | 577-11-7 | Aerosol OT-70 PG |
| Malodor Counteractant | Hydroxypropyl Beta Cyclodextrin | 128446-35-5 | Cavasol |
| Buffer | Sodium Hydroxide | 1310-73-2 | Sodium Hydroxide |
| Equipment | Supplier Name/Model No. | | |
| Balance | Metter Toledo/EP4102, (0.01 resolution) Mettler Toledo/PG503-S (0.001 resolution) | | |
| pH Meter | Thermo Scientific/EO8212 | | |
| Overhead mixing/magnetic stir bar equipment | IKA/RW20 VWR/58947-128 (A variety of stir bars are used dependent on the amount used for the samples- this is one example that can be used) | | |
| Turbidimeter | Hach/2100Q | | |

For the test methods/calculations described hereinafter, any perfume suitable for use in sprayable air fresheners or vapor phase systems may be employed. For illustrative purposes as well as for the subsequent examples for fabric freshening compositions, the perfume may comprise of PRMs as shown in Table 8 below. The perfume, however, may constitute any number of materials suitable for freshening.

TABLE 8

Perfume Samples

| | Perfume Raw Material (PRM) | Perfume Sample 1 (approximately 60% of PRMs ClogP < 3), % by weight of the perfume composition | Perfume Sample 2 (approximately 80% of PRMs ClogP from 1-4.5), % | Perfume Sample 3 (approximately 80% of PRMs ClogP 3-10), % |
|---|---|---|---|---|
| 1 | Ethyl Maltol | 3 | 1.5 | 1 |
| 2 | Helional | 9 | 3 | 2 |
| 3 | HYDROXYCITRONELLAL | 8 | 3 | 2 |
| 4 | Ethyl Vanillin | 3 | 1.5 | 1 |
| 5 | Pyranol | 8 | 3 | 2 |
| 6 | Benzyl acetate | 8 | 3 | 2 |
| 7 | Methyl Phenyl Carbinyl Acetate | 8 | 3 | 2 |

TABLE 8-continued

Perfume Samples

| | Perfume Raw Material (PRM) | Perfume Sample 1 (approximately 60% of PRMs ClogP < 3), % by weight of the perfume composition | Perfume Sample 2 (approximately 80% of PRMs ClogP from 1-4.5), % | Perfume Sample 3 (approximately 80% of PRMs ClogP 3-10), % |
|---|---|---|---|---|
| 8 | Ligustral Or Triplal | 8 | 3 | 2 |
| 9 | Linalool | 8 | 3 | 2 |
| 10 | Cyclo Galbanate | 9 | 3 | 2 |
| 11 | UNDECALACTONE | 2 | 7 | 8 |
| 12 | Citronellol | 8 | 3 | 2 |
| 13 | LINALYL ACETATE | 2 | 7 | 8 |
| 14 | Verdox | 2 | 7 | 8 |
| 15 | 4-tertiary-Butyl cyclohexyl acetate | 2 | 7 | 8 |
| 16 | Orange Terpenes | 2 | 7 | 8 |
| 17 | Ethyl Trimethylcyclopenteene Butenol | 2 | 7 | 8 |
| 18 | Ionone Gamma Methyl | 2 | 7 | 8 |
| 19 | Hexyl salicylate | 2 | 7 | 8 |
| 20 | Habanolide 100% | 2 | 7 | 8 |
| 21 | Iso E super | 2 | 7 | 8 |
| | Total weight of PRMs having a ClogP < 3 | 64 | — | — |
| | Total weight of PRMs having a ClogP 1-4.5 | — | 77.5 | — |
| | Total weight of PRMs having a ClogP 3-10 | | | 84 |
| | Total weight of the perfume composition | 100 | 100 | 100 |

Test Methods

A. Test Method for Measurement of NTU Turbidity

A turbidimeter is used to determine how well ingredients are able to solubilize and emulsify perfume. The method of measuring turbidity is described in detail in the following reference: Hach Company, 2009, 2013., "Hach 2100Q and 2100Q is User Manual." This method of measurement determines quantitative values of turbidity by evaluating the ratio of a primary nephelometric light scatter signal to a transmitted light scatter signal. This particular method of evaluation provides values between 0 to 1000 Nephelometric Turbidity Units ("NTU"), where increasing NTU values indicate more turbid solutions. Thus, successful perfume emulsification will yield lower NTU values vs. unsuccessful perfume emulsification will yield higher NTU values. In between each test sample, water controls should be measured to ensure proper equipment operation.

B. Method for Calculation of Average Value of a of an Ethoxylated Aromatic

This is a method for calculating the average value of a of an ethoxylated aromatic such as for example, an ethoxylated aromatic according to Formula II

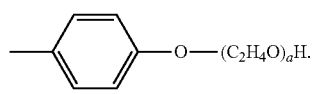

(II)

The individual weight % distributions for each ethoxylated species within an ethoxylated material are used to calculate the average value of a.

$$\text{average } a = \sum_{i=0}^{n} \frac{(x_i * i)}{100}$$

where i is an integer from 0 through n, representing the degree of ethoxylation $x_i$ is the weight % of individual species benzyl alcohol ethoxylate i measured via GCFID method. GCFID refers to known Gas Chromatography Flame Ionization Detection.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A freshening composition comprising:
   a) at least 70% by weight of the freshening composition of water;
   b) a perfume, wherein the perfume comprises at least 60% by weight of the perfume, Perfume Raw Materials having ClogP greater than 1; and
   c) at least 0.0015% by weight of the freshening composition of an alkoxylated aromatic;
   wherein the alkoxylated aromatic is according to Formula (I):

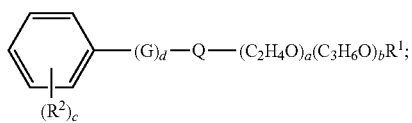

wherein the index d is 0 or 1, and G is selected from $C_1$-$C_4$ alkylene;
wherein Q is selected from O, S, and $NR^3$, where $R^3$ is selected from the group consisting of H, $C_1$-$C_{15}$ alkyl, and $(C_2H_4O)_e(C_3H_6O)_f/R^4$;
wherein a, e individually is a value selected from 1-30; b, f individually is a value selected from 0-15 and b is non-zero;
wherein the value of a+b, the degree of alkoxylation, is from 3 to 30 when Q is O, S or $NR^3$ and $R^3$ is H or $C_1$-$C_{15}$ alkyl,
wherein the value of a+b, the degree of alkoxylation, is from 1 to 20 when Q is $NR^3$ and $R^3$ is $(C_2H_4O)_e(C_3H_6O)/R^4$;
wherein the value of e+f the degree of alkoxylation, is from 1 to 20 when Q is $NR^3$ and $R^3$ is $(C_2H_4O)_e(C_3H_6O)/R^4$;
wherein $R^1$, $R^4$ is independently selected from H and $C_1$-$C_4$ alkyl;
wherein c is a value selected from 0 to 5;
wherein each $R^2$ is independently selected from $C_1$-$C_2$ alkyl, $C_1$-$C_2$ alkoxy, and wherein any two vicinal $R^2$ may combine to make an aliphatic or aromatic fused ring;
wherein when Q is O and $R^1$ is H, at least one of c or d is greater than 0.

2. The composition of claim 1, wherein when Q is O; G is $CH_2$ when d is 1; when d is 1, the index c is 0, 1 or 2; when d is 0, the index c is 1 or 2; when the index c is 1, $R^2$ is $C_1$ alkyl or $C_1$ alkoxy, and when c is 2, two vicinal groups combine to form a fused $C_6$ aromatic ring.

3. The composition of claim 1 wherein the ethoxylate group and the propoxylate group are present in any order.

4. The composition of claim 1, wherein the alkoxylated aromatic is in an amount of at least 0.0015%, by weight of the freshening composition.

5. The composition according to claim 1, wherein the water is in an amount from 70% to 99.5%, by weight of the freshening composition.

6. The composition according to claim 1, further comprising less than 3.5%, of a surfactant by weight of the freshening composition; wherein the surfactant is selected from the group consisting of: nonionic surfactants, cationic surfactants, amphoteric surfactants, zwitterionic surfactants and mixtures thereof.

7. The composition according to claim 1, further comprising less than 10%, of a solvent by weight of the freshening composition, wherein the solvent is selected from the group consisting of: an alcohol, a polyol and mixtures thereof.

8. The composition according to claim 7, wherein the solvent is ethanol, wherein the ethanol is in an amount of less than 10%, by weight of the freshening composition, wherein the combination of ethanol and alkoxylated aromatic define a solvent system.

9. The composition according to claim 7, wherein the composition is substantially free of the solvent.

10. The composition according to claim 1 further comprising a malodor counteractant, wherein the malodor counteractant is selected from the group consisting of: polyols, cyclodextrin and derivatives thereof, amine functional polymers, aldehydes, and combinations thereof.

11. The composition of claim 1, wherein the perfume is in an amount of at least 0.001%, weight of the freshening composition.

12. The composition according to claim 1, wherein the Perfume Raw Materials having ClogP greater than 1 are selected from the group consisting of: dihydro myrcenol, isonoyl alcohol, citronellol, tetrahydro linalool, tepinyl acetate, geranyl acetate, phenyl ethyl phenyl acetate, lilial (PT Bucinal), vertenex, diphenyl methane, p'cymene, alpha pinene, benzyl salicylate, d-limonene, cis-hexenyl salicylate, hexyl cinnamic aldehyde, cedryl acetate, habanolide, ethyl trimethylcyclopentene butanol, hexyl salicylate, iso e super, ethyl vanillin, helional, undecalactone, ionone gamma methyl, hydroxycitronellal, cyclo galbanate, pyranol, verdox, linalyl acetate, benzyl acetate, methyl phenyl carbinyl acetate, triplal, and mixtures thereof.

13. The composition according to claim 1, wherein the value of a+b is from 5 to 10, wherein at least 80%, by weight of the perfume of perfume raw materials having an ClogP greater than 2.0.

14. The composition according to claim 1, wherein the value of e+f is from 5 to 10, wherein at least 80%, by weight of the perfume of perfume raw materials having an ClogP greater than 2.0.

15. The composition according to claim 1, wherein the total weight ratio of the alkoxylated aromatic to the perfume is 0.01:1 to 20,000:1.

16. The composition according to claim 1, wherein the freshening composition comprises a sulfur-containing pro-perfume.

17. The composition according to claim 16, wherein the sulfur-containing pro-perfume is a C4-C16 thio-damascone.

18. A method of manufacturing a freshening composition according to claim 1, the method comprising:
   i) mixing an alkoxylated aromatic and a perfume to form a pre-mix, wherein the weight ratio of the alkoxylated aromatic to the perfume is 0.01:1 to 100:1;
   ii) adding the pre-mix to the water to form the freshening composition.

19. A non-aerosol freshening sprayer product comprising:
   a plastic container containing a freshening composition according to claim 1, wherein the plastic container is made of plastic selected from the group consisting of: polypropylene, polyethylene terephthalate, high density polyethylene and combinations thereof.

* * * * *